US009370579B2

(12) United States Patent
Jin et al.

(10) Patent No.: US 9,370,579 B2
(45) Date of Patent: Jun. 21, 2016

(54) TEMPLATED NATIVE SILK SMECTIC GELS

(71) Applicant: Trustees of Tufts College, Boston, MA (US)

(72) Inventors: Hyoung-Joon Jin, Seoul (KR); Jae-Hyung Park, Decatur, GA (US); Regina Valluzzi, Arlington, MA (US)

(73) Assignee: Trustees of Tufts College, Boston, MA (US)

( * ) Notice: Subject to any disclaimer, the term of this patent is extended or adjusted under 35 U.S.C. 154(b) by 228 days.

(21) Appl. No.: 14/078,113

(22) Filed: Nov. 12, 2013

(65) Prior Publication Data

US 2014/0155496 A1 Jun. 5, 2014

Related U.S. Application Data

(60) Continuation of application No. 12/536,793, filed on Aug. 6, 2009, now Pat. No. 8,580,924, which is a division of application No. 10/533,611, filed as application No. PCT/US03/34684 on Oct. 31, 2003, now Pat. No. 7,572,894.

(60) Provisional application No. 60/423,046, filed on Nov. 1, 2002.

(51) Int. Cl.
*A61K 47/42* (2006.01)
*C07K 14/435* (2006.01)

(52) U.S. Cl.
CPC ........... *A61K 47/42* (2013.01); *C07K 14/43586* (2013.01); *Y10T 436/25375* (2015.01)

(58) Field of Classification Search
None
See application file for complete search history.

(56) References Cited

FOREIGN PATENT DOCUMENTS

| JP | HEI03-270731 | 12/1991 |
| JP | HEI08-155207 | 6/1996 |
| JP | 2002186847 A | 7/2002 |

OTHER PUBLICATIONS

Ayub, Z. H. et al., "Mechanism of the Gelation of Fibroin Solution", *Biosci. Biotech. Biochem.*, 57(11):1910-1912 (May 24, 1993).
Bunnak, J. et al., "Study on Antibacterial Activity of Hydrogel from Irradiated Silk Protein", *JAERI Conf.*, 117-129 (2001) (Abstract).
Dinerman, A. A. et al., "Swelling behavior of a genetically engineered silk-elastinlike protein polymer hydrogel", *Biomaterials*, 23:4203-4210 (2002).
Hukins, D. W. L. et al., "Collagen Fibrils as Examples of Smectic A Biological Fibres", *Mol. Cryst. Liq. Cryst.*, 41(2):33-40 (Gordon and Breach Science Publishers, Ltd., USA) (1977).
Jin, H.-J. et al., "Biomaterial Films of *Bombyx mori* Silk Fibroin with Poly(ethylene oxide)", *Biomacromolecules*, 5:711-717 (2004).
Valluzzi, R. et al., "*Bombyx mori* silk fibroin liquid crystallinity and crystallization at aqueous fibroin-organic solvent interfaces", *Intern. J. of Biol. Macromol.*, 24:227-236 (Elsevier Science B.V.)(Mar. 1999).
Zhang, Y.-Q., "Applications of natural silk protein sericin in biomaterials", *Biotechnology Advances*, 20:91-100 (2002).
International Search Report dated Jul. 2, 2004.

*Primary Examiner* — Anand Desai
(74) *Attorney, Agent, or Firm* — Dana M. Gordon; Foley Hoag LLP

(57) ABSTRACT

One aspect of the present invention relates to a method of preparing a fibrous protein smectic hydrogel by way of a solvent templating process, comprising the steps of pouring an aqueous fibrous protein solution into a container comprising a solvent that is not miscible with water; sealing the container and allowing it to age at about room temperature; and collecting the resulting fibrous protein smectic hydrogel and allowing it to dry. Another aspect of the present invention relates to a method of obtaining predominantly one enantiomer from a racemic mixture, comprising the steps of pouring an aqueous fibrous protein solution into a container comprising a solvent that is not miscible with water; sealing the container and allowing it to age at about room temperature; allowing the enantiomers of racemic mixture to diffuse selectively into the smectic hydrogel in solution; removing the smectic hydrogel from the solution; rinsing predominantly one enantiomer from the surface of the smectic hydrogel; and extracting predominantly one enantiomer from the interior of the smectic hydrogel. The present invention also relates to a smectic hydrogel prepared according to an aforementioned method.

7 Claims, 33 Drawing Sheets

1           2

1

2

3

- Long homogeneous helical domains
- Not necessarily "folded"
- Polymorphic secondary structure
- Material formed by mesophase
- Structural role
- Extended fibers or fibrils
- –similar to synthetic polymers
- –can be polycrystalline, mineralized

- "Liquid Crystal"
  – Molecules anisotropic
  – orientation, possibly some position Chiral one dimensional liquid crystal Two dimensional liquid crystals 1. Nanocomposite - nanodomains of one phase separated by nanoscale domains of a second phase 2. Simple Patterned Nanocomposite (from smectic layers)

3. "Cocrystal" - peptide phase crystallizes and/or inorganic phase crystallizes within layers Silkworm Reciprocal Lattice for
Cholesteric Film Cholesteric
Diffraction
Pattern
Expected Peptide (GAGAGS) core Met triggered Spider silk (biosynthetic)

Peptides                                            Native Proteins (silks)

Air water interface from EDTA-Na aqueous solution of $(Glu)_5(Gly\text{-}Asp\text{-}Val\text{-}Gly\text{-}Gly\text{-}Ala\text{-}Gly\text{-}Ala\text{-}Thr\text{-}Gly\text{-}Gly\text{-}Ser)_2(Glu)_5$

- A designed helix with a stronger hydrophobic/hydrophilic difference will be more readily stabilized and anchored parallel to the interface
- Helical axis is perpendicular to smectic layer plane
- Helices which tend to be parallel to interface and film result in layers more often normal to film

TEMPLATED NATIVE SILK SMECTIC GELS

RELATED APPLICATIONS

This application is a continuation of U.S. patent application Ser. No. 12/536,793, filed Aug. 6, 2009, now U.S. Pat. No. 8,580,924, which is a divisional of U.S. patent application Ser. No. 10/533,611, filed May 11, 2006, now U.S. Pat. No. 7,572,894; which claims the benefit of priority under 35 USC section 371 to Patent Cooperation Treaty Application serial number PCT/US2003/034684, filed Oct. 31, 2003; which claims the benefit of priority to U.S. Provisional Patent Application Ser. No. 60/423,046, filed Nov. 1, 2002.

GOVERNMENT SUPPORT

The invention was made with support provided by NASA (grant NAGS-1699) and NSF (grant BES 9727401); therefore, the government has certain rights in the invention.

BACKGROUND OF THE INVENTION

There are broadly three different types of liquid crystalline material: nematic, cholesteric, and smectic. The types are distinguished by differences in molecular ordering. Such materials only show a liquid crystal phase over a limited temperature range between the solid and isotropic liquid phases. Within the liquid crystal phase temperature range, a material may exhibit one or more of the nematic, cholesteric or smectic phase types. Normally, a material is chosen such that it forms only one type of liquid crystal phase over its working temperature range.

Liquid crystalline elastomers combine the various broken symmetries of liquid crystalline phases with the elasticity of polymer networks. One obvious effect is that the single crystal elastomers can undergo spontaneous shape changes when they undergo a liquid crystalline transition. There are many more subtle effects in the interplay between the fluctuations of the familiar liquid crystalline and elastic degrees of freedom (for example, and perfect single crystal nematic elastomer can, in theory, exhibit elastic moduli of zero when deformed in certain directions. These dramatic effects are, of course, drastically influenced by the disorder, which makes them perfect for studying quenched disorder.

Biopolymer networks are found all over nature. For example, the cytoskeleton is supported by a network of actin, which is a semi-flexible polymer with globular proteins as a monomer unit. These networks are proving to be ideal model systems for understanding the physics of semi-flexible polymers, both in solution and cross-linked network states.

The fibrous proteins can be considered to be a special class of proteins that serve important structural functions in the extracellular environment. In living organisms some of these proteins, such as collagens, are found in thin layers, sandwiched between other extracellular biomaterials. When studying the physical chemistry of extracellular fibrous proteins in vitro the use of a two-dimensional thin film or interfacial environment will help the proteins self-assemble more efficiently by providing a restricted environment in comparison to three-dimensional bulk systems. It is thus beneficial to study the synergistic interaction between the behavior of fibrous proteins in dimensionally restricted environments (such as thin films or two-dimensional layers) and the generation of structure and long range order through self-assembly.

Different conformations can be stabilized by an interface, such as an extended chain β-sheet conformation, which maximizes the protein's spreading and surface area. If the protein or model polypeptide has hydrophobic side chains, and can readily take on a stable a-helical conformation, α-helices will be stable at the interface. Biridi, K. S. *Journal of Colloid and Interface Science* 1973, 43, 545; Cheesman, D. F.; Davies, J. T. *Advan. Protein Chem.* 1954, 9, 439; Jacuemain, D.; Wolf, S. G.; Leveiller, F.; Lahav, M.; Leiserowitz, L.; Deutsch, M.; Kjaer, K.; Als-Nielsen, J. *Journal of the American Chemical Society* 1990, 112, 7724-7736; Loeb, G. I. *Journal of Colloid and Interface Science* 1968, 26, 236; Loeb, G. I. *Journal of Colloid and Interface Science* 1969, 31, 572; Macritchie, F. *Adv. Coll. Int. Sci.* 1986, 25, 341-382; Magdassi, S.; Garti, N. *Surface Activity of Proteins*; Magdassi, S.; Garti, N., Ed.; Marcel Dekker: New York, 1991; Vol. 39, pp 289 -300; Malcolm, B. R. *Nature* 1962, 4195, 901; Malcolm, B. R. *Soc. Chem. Ind. London* 1965, 19, 102; Malcolm, B. R. *Progress in Surface and Membrane Science* 1971, 4, 299; Murray, B. S. *Coll. Surf. A* 1997, 125,73-83; Murray, B. S.; Nelson, P. V. *Langmuir* 1996, 12, 5973-5976; Weissbuch, I.; Berkovic, G.; Leiserowitz, L.; Lahav, M. *Journal of the American Chemical Society* 1990, 112, 5874-5875; Wustneck, R.; Kragel, J.; Miller, R.; Wilde, P. J.; Clark, D. C. *Coll. Surf. A* 1996, 114, 255-265. The influence of side chain character in stabilizing an interfacial conformation suggests that hydropathicity can be used as a determinant for interfacial conformation. Carrying this idea further, if a sequence of residues results in particular conformations that could exhibit surfactant behavior, these conformations should be stabilized at an interface.

Silks, and their analogues, have recently been the focus of interest for applications in biomaterials because of the intriguing properties of the silk fiber. The simplicity of their sequences lends them to be used as model fibrous proteins. Most of the studies on the properties of silks, as well as other fibrous proteins either examine gross materials properties such as mechanical properties, thermal stability and surface roughness or examine very localized chemical details in the molecule. Literature on long-range ordered "helicoids" is less abundant.

Previously we have disclosed that with *B. mori* silk fibroin, a threefold helical polyglycine II or polyproline II type of conformation was stabilized by the interface, even though it is not observed in bulk. Valluzzi, R.; Gido, S. P. *Biopolymers* 1997, 42, 705-717; Valluzzi, R.; Gido, S.; Zhang, W.; Muller, W.; Kaplan, D. *Macromolecules* 1996, 29, 8606-8614; Zhang, W.; Gido, S. P.; Muller, W. S.; Fossey, S. A.; Kaplan, D. L. *Electron Microscopy Society of America, Proceedings* 1993, 1216. The *B. mori* fibroin crystallizable sequence is approximately $(Gly-Ala-Gly-Ala-Gly-Ser)_x$, and a left-handed threefold helical conformation, which is sterically reasonable, separates hydrophobic alanine and hydrophilic serine residues to opposite sides of the interface. Valluzzi, R.; Gido, S. P. *Biopolymers* 1997, 42, 705-717; Valluzzi, R.; Gido, S.; Zhang, W.; Muller, W.; Kaplan, D. *Macromolecules* 1996, 29, 8606-8614; Zhang, W.; Gido, S. P.; Muller, W. S.; Fossey, S. A.; Kaplan, D. L. *Electron Microscopy Society of America, Proceedings* 1993, 1216.

As a consequence of the difficulties entailed in attempting detailed surface measurements at a liquid-liquid interface, there have been few studies on the behavior of proteins at these interfaces to date. Murray and Nelson, working with a novel oil-water trough design, have published results on the comparative behavior of β-lactoglobulin and bovine serum albumin (both globular) protein films at air-water and oil-water interfaces that appear consistent with structural results obtained for fibrous proteins at air-water and oil-water interfaces. Murray, B. S. *Coll. Surf. A* 1997, 125, 73-83; Murray, B. S.; Nelson, P. V. *Langmuir* 1996, 12, 5973-5976. They found that films at the oil-water interface were more expanded and also more expansible and compressible than corresponding films at the air-water interface. This was believed to be due to a reduction in aggregation. The increased solubility of the hydrophobic groups in oil as opposed to air is cited as a reason for the greater stability of films at the oil-water interface. Shchipunov has studied phospholipids at an oil water interface, and observed that the presence of the amphiphiles results in more oil on the water side of the interface and more water on the oil side. Shchipunov, Y. A. *Liquid/Liquid Interfaces and Self-Organized Assemblies of Lecithin*; Shchipunov, Y. A., Ed.; CRC Press: Boca Raton, Fla., 1996, pp 295-315. The amphiphile compatibilizes the two liquids forming the interface, and in the process, the interface thickens. Both the compatibilization effect observed for the phospholipids and the stability observed for the protein films suggest that there is oil and water closely interacting with the side chains of the protein. Side chain—side chain interactions would thus be expected to be screened. Jacuemain, D.; Wolf, S. G.; Leveiller, F.; Lahav, M.; Leiserowitz, L.; Deutsch, M.; Kjaer, K.; Als-Nielsen, J. *Journal of the American Chemical Society* 1990, 112, 7724-7736; Malcolm, B. R. *Nature* 1962, 4195, 901; Murray, B. S. *Coll. Surf. A* 1997, 125, 73-83; Murray, B. S.; Nelson, P. V. *Langmuir* 1996, 12, 5973-5976; Wustneck, R.; Kragel, J.; Miller, R.; Wilde, P. J.; Clark, D. C. *Coll. Surf. A* 1996, 114, 255-265; Shchipunov, Y. A. *Liquid/Liquid Interfaces and Self-Organized Assemblies of Lecithin*; Shchipunov, Y. A., Ed.; CRC Press: Boca Raton, Fla., 1996, pp 295-315; Miller, I. R. *Progress in Surface and Membrane Science* 1971, 4, 299.

An aqueous-hexane interface was chosen as an initial probe of fibroin liquid-liquid interface behavior. This interface, in the absence of fibroin, is believed to be about 10 Å thick. Carpenter, I. L.; Hehre, W. J. *Journal of Physical Chemistry* 1990, 94, 531-536; Michael, D.; Benjamin, I. *Journal of Physical Chemistry* 1995, 99, 1530-1536. The silk at the aqueous-hexane interface forms a film as it ages, and this film can be picked up onto sample grids for observation in a transmission electron microscope (TEM). The hexane was expected to be a better solvent for the alanine residues in silk than the water, forcing them to the hexane side of the interface. The aqueous phase should be a better solvent for serine.

SUMMARY OF INVENTION

In one embodiment, the present invention relates to a method of preparing a fibrous protein smectic hydrogel by way of a solvent templating process comprising the steps of:
a. pouring an aqueous fibrous protein solution into a container comprising a solvent that is not miscible with water;
b. sealing the container and allowing it to sit at about room temperature overnight; and
c. collecting the resulting fibrous protein smectic hydrogel and allowing it to dry.

In a further embodiment, the present invention relates to the above solvent templating process, wherein the solvent is chloroform.

In a further embodiment, the present invention relates to the above solvent templating process, wherein the solvent is iso-amyl alcohol.

In a further embodiment, the present invention relates to the above solvent templating process, wherein the solvent is hexane.

In a further embodiment, the present invention relates to the above solvent templating process, wherein the fibrous protein is selected from the group consisting of silk, collagens, keratins, actins, chorions, and seroins.

In a further embodiment, the present invention relates to the above solvent templating process, wherein the fibrous protein is silk.

In a further embodiment, the present invention relates to the above solvent templating process, wherein the fibrous protein solution is greater than about 4% by weight.

In a further embodiment, the present invention relates to the above solvent templating process, wherein the fibrous protein solution is greater than about 8% by weight.

In a further embodiment, the present invention relates to the above solvent templating process, wherein the fibrous protein solution is greater than about 4% by weight, the fibrous protein is silk, and the solvent is iso-amyl alcohol.

In a further embodiment, the present invention relates to the above solvent templating process, wherein the fibrous protein solution is greater than about 8% by weight, the fibrous protein is silk, and the solvent is iso-amyl alcohol.

In a further embodiment, the present invention relates to the above solvent templating process, wherein the fibrous protein solution is greater than about 4% by weight, the fibrous protein is silk, and the solvent is chloroform.

In a further embodiment, the present invention relates to the above solvent templating process, wherein the fibrous protein solution is greater than about 8% by weight, the fibrous protein is silk, and the solvent is chloroform.

In a further embodiment, the present invention relates to the above solvent templating process, wherein the fibrous protein solution is greater than about 4% by weight, the fibrous protein is silk, and the solvent is hexane.

In a further embodiment, the present invention relates to the above solvent templating process, wherein the fibrous protein solution is greater than about 8% by weight, the fibrous protein is silk, and the solvent is hexane.

In another embodiment the present invention relates to a method of obtaining predominantly one enantiomer from a racemic mixture, comprising the steps of:
a. pouring an aqueous fibrous protein solution into a container comprising a solvent that is not miscible with water;
b. sealing the container and allowing it to sit at about room temperature overnight;
c. allowing the racemic mixture to diffuse into the smectic hydrogel in solution;
d. removing the smectic hydrogel from the solution;
e. rinsing predominantly one enantiomer from the surface of the smectic hydrogel; and
f. extracting predominantly one enantiomer from the interior of the smectic hydrogel.

In a further embodiment, the present invention relates to the above method of obtaining predominantly one enantiomer, wherein the fibrous protein is selected from the group consisting of silk, collagens, keratins, actins, chorions, and seroins.

In a further embodiment, the present invention relates to the above method of obtaining predominantly one enantiomer, wherein the fibrous protein is silk.

In a further embodiment, the present invention relates to the above method of obtaining predominantly one enantiomer, wherein the fibrous protein solution is greater than about 4% by weight.

In a further embodiment, the present invention relates to the above method of obtaining predominantly one enantiomer, wherein the fibrous protein solution is greater than about 8% by weight.

In a further embodiment, the present invention relates to the above method of obtaining predominantly one enantiomer, wherein the fibrous protein solution is greater than about 4% by weight and the fibrous protein is silk.

In a further embodiment, the present invention relates to the above method of obtaining predominantly one enantiomer, wherein the fibrous protein solution is greater than about 8% by weight and the fibrous protein is silk.

In another embodiment, the present invention relates to the fibrous protein smectic hydrogel prepared by the above solvent templating method.

In a further embodiment, the present invention relates to the fibrous protein smectic hydrogel prepared by the above solvent templating method, wherein the fibrous protein is selected from the group consisting of silk, collagens, keratins, actins, chorions, and seroins.

In a further embodiment, the present invention relates to the fibrous protein smectic hydrogel prepared by the above solvent templating method, wherein the fibrous protein is silk.

In a further embodiment, the present invention relates to the fibrous protein smectic hydrogel prepared by the above solvent templating method, wherein the fibrous protein smectic hydrogel is greater than or equal to about 38 nm thick.

DETAILED DESCRIPTION OF THE INVENTION

Definitions

Figure 1:
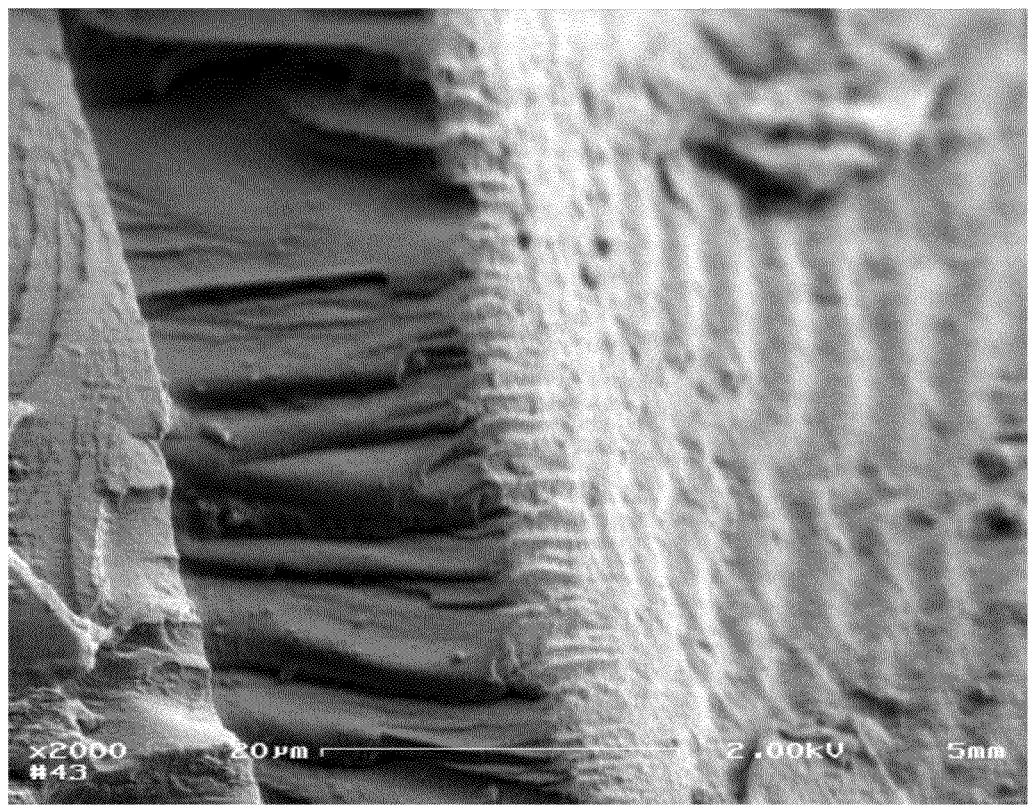
FIG. 1 depicts the surface (right) and fracture surface of chloroform templated silk. The wavy texture is everywhere on the solvent templated side of the materials surface.
Figure 2:
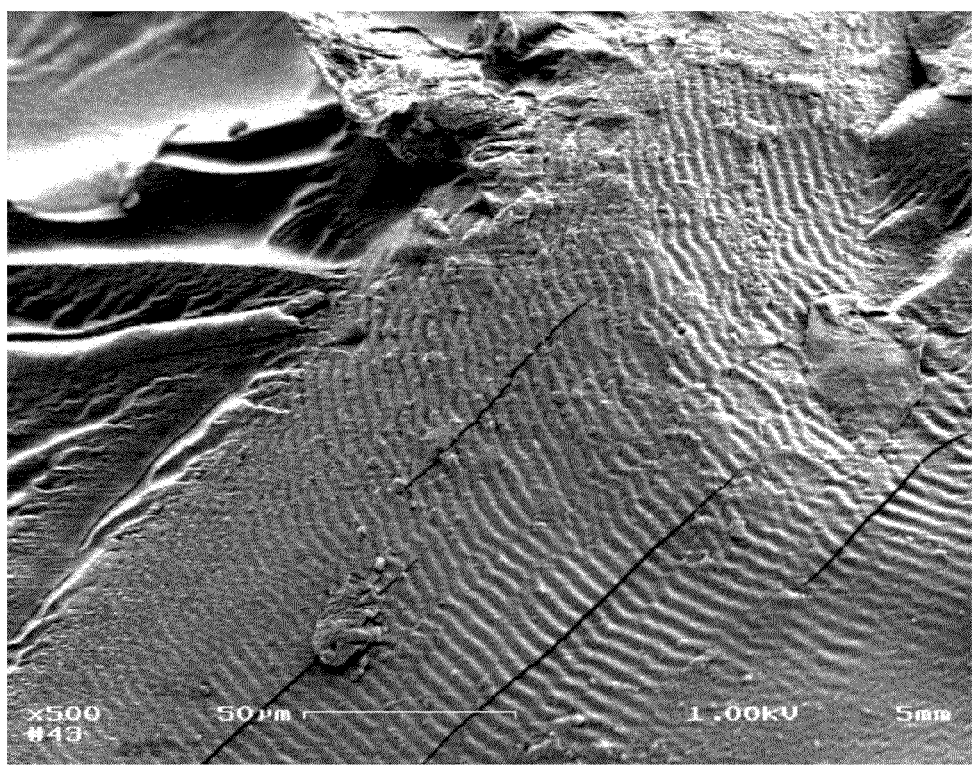
FIG. 2 depicts the chloroform templated film. Waves reorienting and becoming terraces can be seen, behavior which is not expected for simple wrinkles due to contraction.
Figure 3:
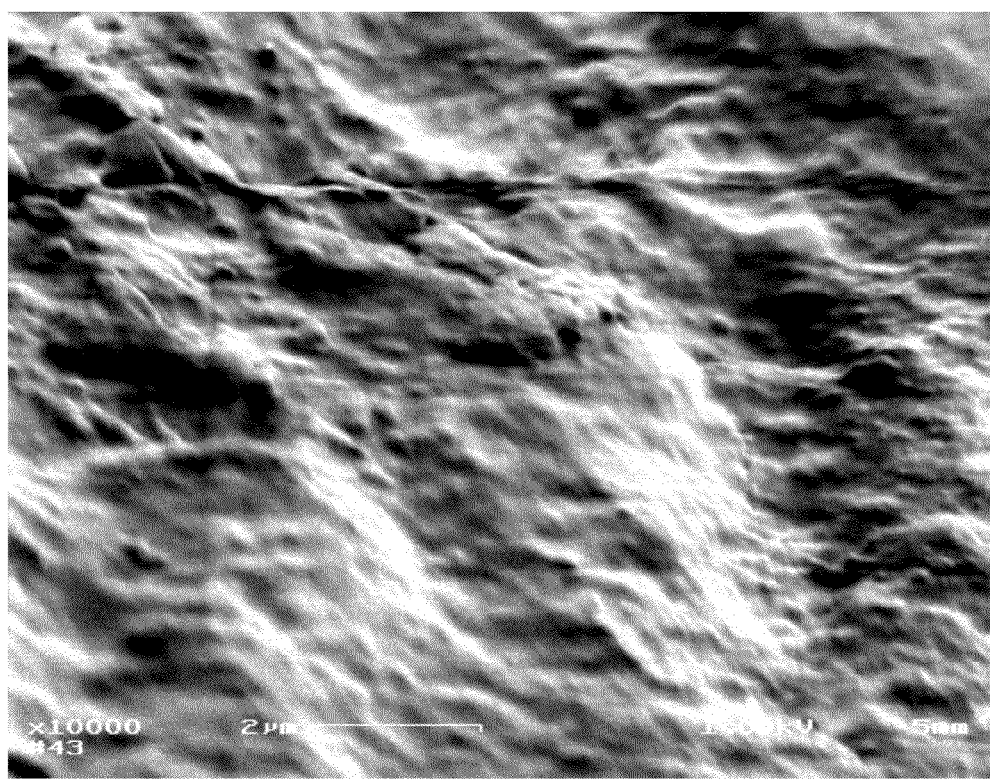
FIG. 3 depicts a regular pattern of nubby small structures comprising the waves.
Figure 4:
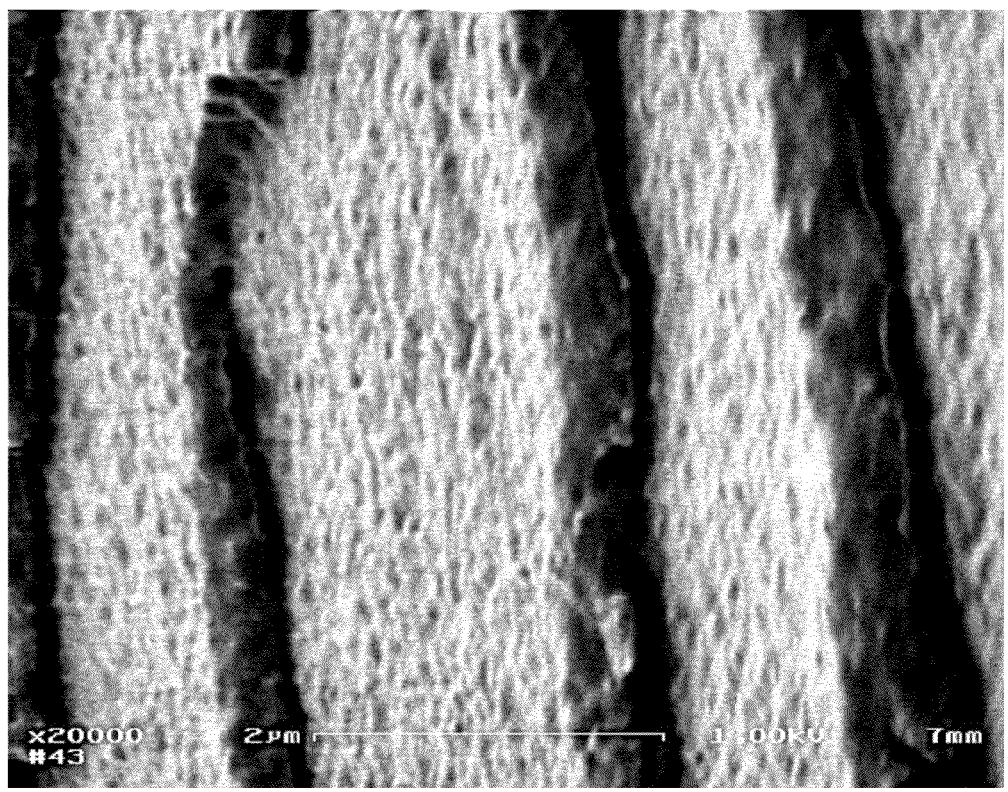
FIG. 4 depicts an amyl alcohol film showing a surface that looks like a "nonwoven woven" fabric.
Figure 5:
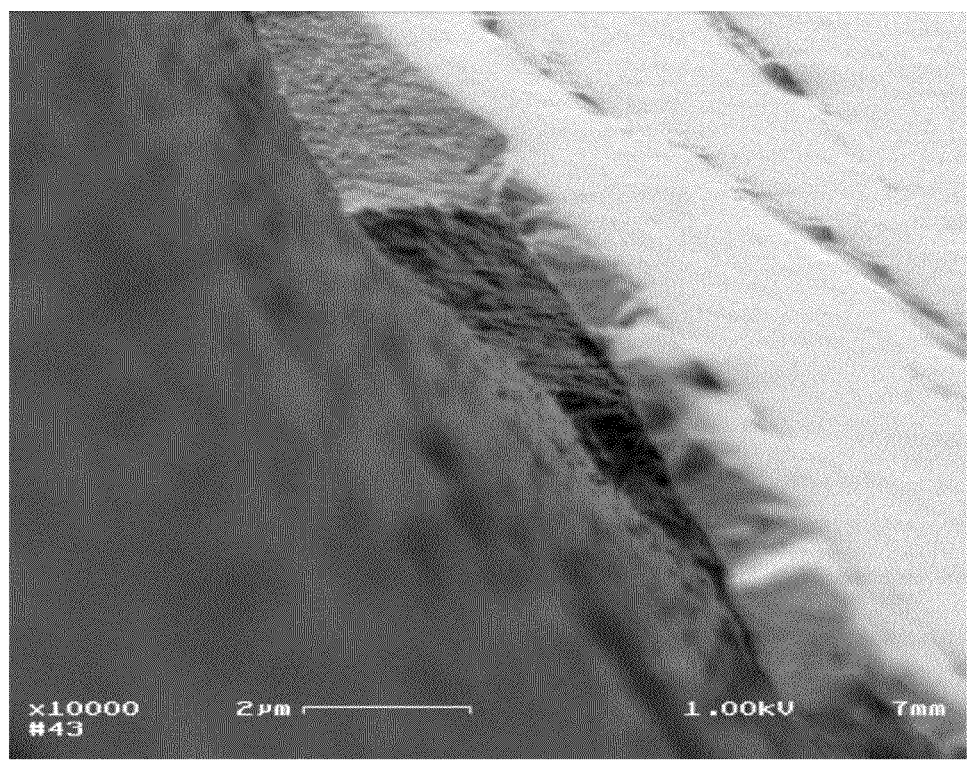
FIG. 5 depicts a surface texture seen at an angle showing a thin layer very different from the chloroform films.
Figure 6:
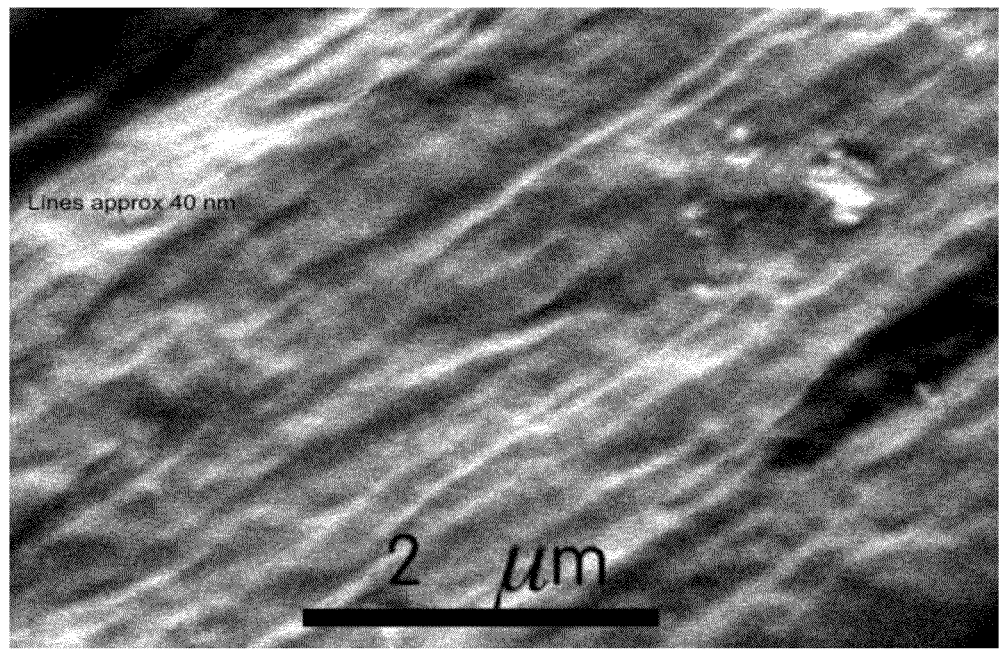
FIG. 6 depicts amyl alcohol templated samples soaked in bipyridyl trisRull chloride hexahydrate giving a high magnification image and a 40 nm layered feature.
Figure 7:
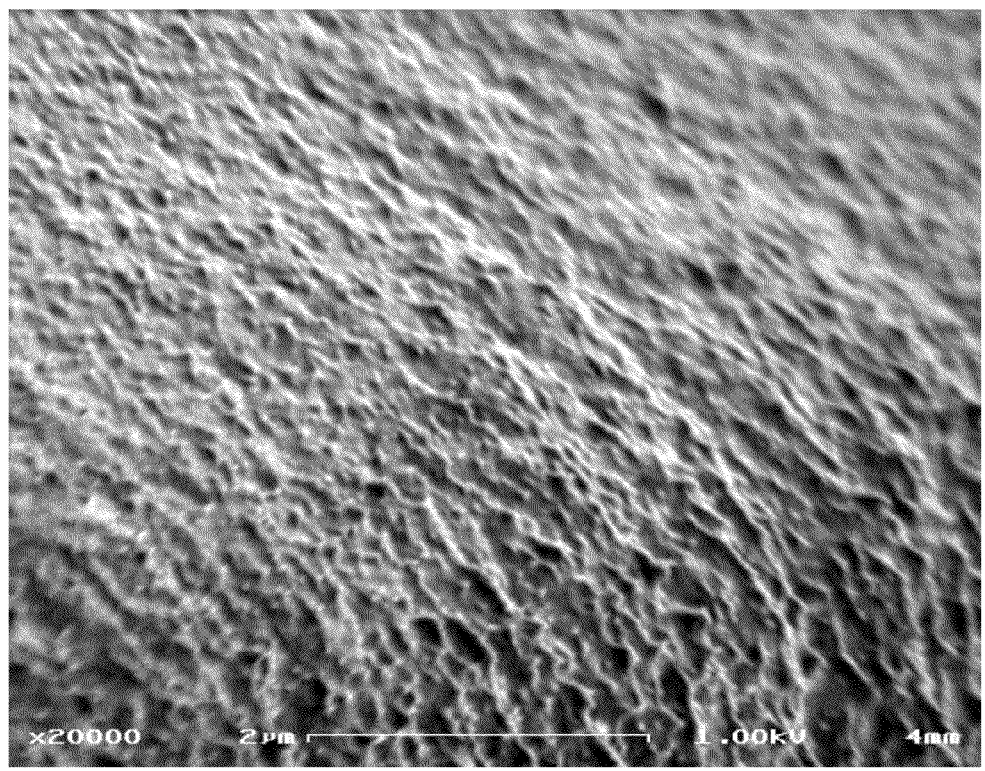
FIG. 7 depicts films after soaking in a dysprosium chloride solution for added contrast. The wavy layered structure of the chloroform templated film is apparent here.
Figure 8:
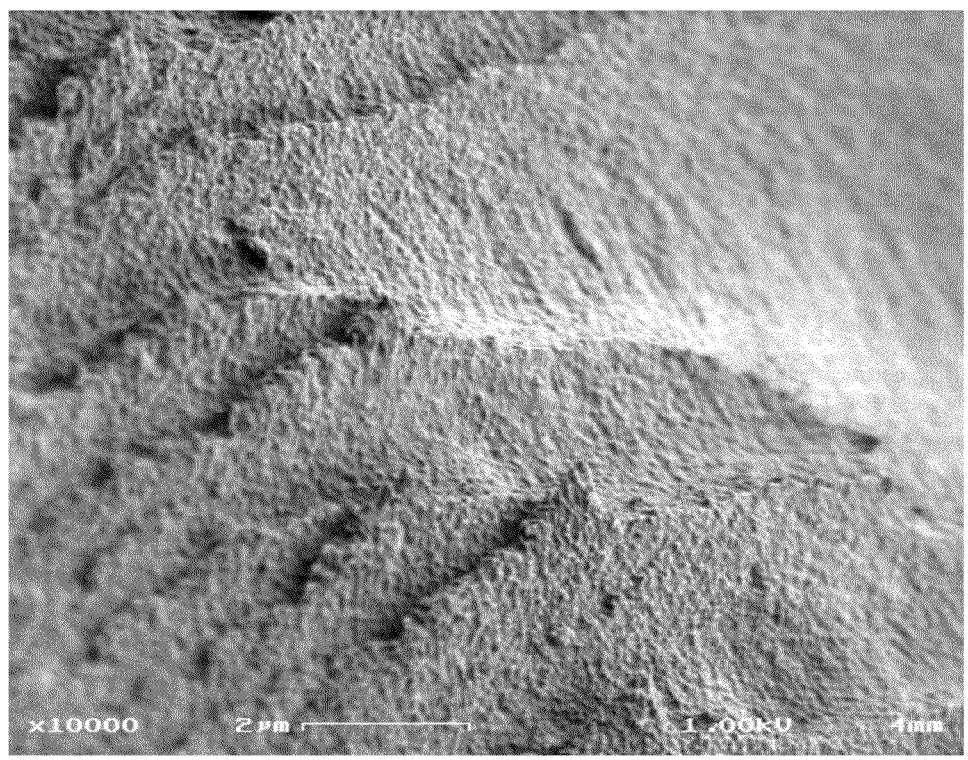
FIG. 8 depicts a film's texture that is even and regular.

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used to mean "including but not limited to". "Including" and "including but not limited to" are used interchangeably.

The term "smectic" is art-recognized and refers to the mesomorphic phase of a liquid crystal in which molecules are closely aligned in a distinct series of layers, with the axes of the molecules lying perpendicular to the plane of the layers.

The term "gel" is art-recognized and refers to a colloid in which the disperse phase has combined with the dispersion medium to produce a semisolid material.

The term "hydrogel" is art-recognized and refers to a colloid in which the particles are in the external or dispersion phase and water is in the internal or dispersed phase.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, azetidine, azepine, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

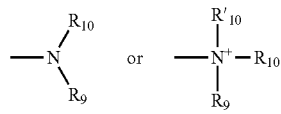

wherein R$_9$, R$_{10}$ and R'$_{10}$ each independently represent a group permitted by the rules of valence.

The term "acylamino" is art-recognized and refers to a moiety that can be represented by the general formula:

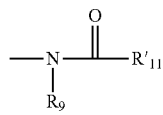

wherein R$_9$ is as defined above, and R'$_{11}$ represents a hydrogen, an alkyl, an alkenyl or —(CH$_2$)$_m$—R$_8$, where m and R$_8$ are as defined above.

The term "amido" is art recognized as an amino-substituted carbonyl and includes a moiety that can be represented by the general formula:

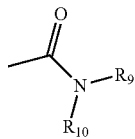

wherein R$_9$, R$_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

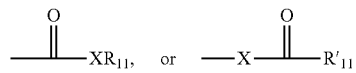

wherein X is a bond or represents an oxygen or a sulfur, and R$_{11}$ represents a hydrogen, an alkyl, an alkenyl, —(CH$_2$)$_m$—R$_8$ or a pharmaceutically acceptable salt, R'$_{11}$ represents a hydrogen, an alkyl, an alkenyl or —(CH$_2$)$_m$—R$_8$, where m and R$_8$ are as defined above. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiolcarbonyl" group. Where X is a sulfur and R$_{11}$ or R'$_{11}$ is not hydrogen, the formula represents a "thiolester." Where X is a sulfur and R$_{11}$ is hydrogen, the formula represents a "thiolcarboxylic acid." Where X is a sulfur and R$_{11}$' is hydrogen, the formula represents a "thiolformate." On the other hand, where X is a bond, and R$_{11}$ is not hydrogen, the above formula represents a "ketone" group. Where X is a bond, and R$_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and R$_8$ are described above.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo undesired transformation, such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, it may be isolated using chiral chromatography methods, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

For purposes of this invention, the chemical elements are identified in accordance with the Periodic Table of the Elements, CAS version, Handbook of Chemistry and Physics, 67th Ed., 1986-87, inside cover.

Fibrous-Protein Smectic Hydrogels

We have demonstrated control over helicoid structure—the material superstructure generated by an array of twisting molecules (like a chiral liquid crystal) in a model fibrous protein (silk). The processes used are very simple and can be applied easily elsewhere to create nanostructured "designer" biomaterials for studies in areas ranging from cell biology and surface interactions to surface nanofluidics. These simple processes were carefully designed using what we know about fibrous proteins (as different from synthetic polymers and globular proteins), and their success underscores the possibilities for manipulating these molecules with processes that are tailored for fibrous proteins (rather than using polymer techniques that destroy their structure, or trying to get them to behave like globular proteins). The characterization results highlight a few key features that distinguish the nature of these proteins.

Remarkably, two processes have been developed that allow the creation of highly structured biomaterials from regenerated silks. A silk solubilization process has been modified to obtain concentrations in excess of 8 wt % silk in aqueous solution. An earlier process yields purified silk solutions of up to only about 4-5 wt %, depending on the purity of the solution and freshness of the raw silk used. A solvent templating process yields nanostructured permselective materials from aqueous silk solutions with concentrations of >about 4 wt %. In general the solvent templating process yields thicker, bulk solids with the thin film features (many layers stacked up) when using about an 8 wt % aqueous silk solution as opposed to about a 4 wt % solution which yields a thin film. In tandem, these two discoveries allow the creation of protein membranes, films, and gels which are made of discrete stacks of protein layers which can be about 38 nm or thicker. Wrinkling and perforation of these layers, combined with chiral stacking interactions (a tendency to twist) result in a number of different very regular microscale patterned surface textures. Many of the films selectively absorb small molecules and ions from solution, and many are chirally selective as well. Thus they may find application as therapeutic agent delivery materials, components in a chiral separations process, matrices for chiral enzymes and catalysts, and as chiral templates. The morphology and microstructure of the films can be controlled by choice of solvent, starting concentration of protein, and environmental factors such as temperature, humidity, addition of ether and/or alcohol to the protein solution, addition of acid to the protein solution, or addition of divalent ionic salts to the protein solution. Altering these parameters results in different permeation properties for the protein materials, different molecular orientations observed within the films, and different surface topographies. The length scale of the topographic features and the protein nature of the films also suggests applications in tissue engineering and cell biology, where microscale and nanoscale patterns have been shown to strongly influence cell growth, differentiation, and tumogenesis. The data gathered to date suggest that the materials may be chemically patterned as well, allowing bioactive sites and molecules to be precisely placed on the material surface and throughout the material. This arrangement would result in extremely predictable and reproducible diffusion rates out of the material for therapeutic agent delivery applications, as well as suggesting novel surgical materials patterned to address cellular processes involved in healing. The material fabrication process is based on chemical and physical features common to many fibrous protein molecules such as collagens, keratins, actins, chorions, seroins, and other silks. Many of these features are also found in non-protein biopolymers such as cellulose, many polysaccharides, and nucleic acids. We would thus expect the process to be useful in making patterned biocompatible nanomaterials from a large number of natural molecules in addition to silks.

Silk-Based Smectic Gels

Concentrated solutions (in general about 4 wt % for thin films, about 8 wt % for bulk solids comprising several layers stacked up) of silk can be used to grow hydrogels from an aqueous organic, liquid-liquid interface. For example, a silk solution is placed into a vessel, a solvent such as chloroform, hexane, or amyl alcohol is carefully layered on top of the silk solution (underneath in the case of chloroform, which is denser than aqueous solutions). The layered liquid is covered to prevent evaporation and excessive competing interactions with air, and a film forms at the interface. In the case of bulk solid hydrogels, the film grows into the aqueous silk phase. Solvent templated processing of natural silks results in the formation of a nanolayered structure, where the layer thickness and chemistry within the layers is determined by the folding pattern induced in the silk molecules (or other fibrous protein molecules) through processing. The nanolayered protein material structure is obtained from high concentration solutions of protein, where the molecule and solution may have locally ordered structure prior to templating.

Highly structured templated solid materials cannot be obtained for silks below concentrations of about 4 wt % protein, and the most organized and oriented structured materials are obtained from solutions with protein concentrations of greater than about 5 wt %. Furthermore, standard film casting techniques do not yield ordered solids, even when the starting solutions contain about 5-8 wt % protein. The choice of solvent used in templating is also important. Solvents which are not at all miscible in water, such as hexane, do not template hydrogels, but instead form viscous liquid crystalline films which are localized in a very thin region at the interface. Solvents which do not have a greater affinity than water for some of the side chains in silk (or other protein used) do not result in templating behavior. An example is dichloroethane, which has a low affinity for both the polar and nonpolar side chains in a typical protein and exhibits no surface templating behavior. Solvents which are somewhat miscible in water, or which make a low energy interface with water are weakly templating. For example, using propanol and butyl alcohol with a silk solution results in a loose, poorly localized gel, due to the large thickness and weak chemical gradient in the interfacial region. Dried material from these gels is poorly oriented, not well-ordered, and either does exhibit the pronounced permselective properties and microstructure observed in templated films, although weak versions of these properties are sometimes observed.

The choice of salt in the aqueous silk solution is also important. A switch from LiSCN to LiBr enabled the preparation of the higher concentrated silk aqueous solution used for templating ordered bulk solids.

The result of a molecular design which consists of a large self-fabricating unit and smaller solubilizing/functional ends, is that the thermodynamically favorable state for the entire molecule will be similar to the thermodynamically favorable state for the self-fabricating block. There may be a structural compromise due to the presence of the end blocks, but since the fabricating block dominates the mass and volume of the molecule these compromises are expected to be minor However, the situation for the solubilizing/functional end blocks is quite different. In a molecular packing geometry dominated by interaction between self-fabricating blocks the local packing in regions containing chain ends will often be highly strained due to thermodynamic frustration. If the ideal thermodynamically favorable geometry for the end blocks is not compatible with the packing favored by the self fabricating blocks (which comprise most of the molecule) the end blocks will be forced into a state that is far from their (local) thermodynamic ideal, and will be "frustrated". By designing multiblock "miniblock" oligomers with block to block disparities in residue size, volume, preferred conformation, etc. we can design frustrated smectically ordered solids, where the density and interaction behavior in the interlayer region is strongly perturbed with respect to bulk material or non-frustrated surfaces with the same composition.

The use of smectic forming self-fabricating blocks, oligomeric molecular weight and associated liquid to solid transitions, and a nanoscopic designed frustrated interlayer region (from end blocks) allows us to construct molecularly designed materials with nanoscale fluid channels. These channels are essentially the endblock-rich regions in the multilayered smectic generated structures. Through engineered mismatching of the properties of monomers used to specify the end blocks vs. the self-fabricating blocks, different properties in these channels can be designed in. The regions in question contain chain ends and are thus somewhat less constrained than the regions comprised of self-fabricating blocks. The chain ends protruding into the interlayer region create a brush at the molecular scale. Molecules absorbed into the miniblock derived material will migrate preferentially into the interlayer regions because:

1. Space exists or can be made to accommodate additional molecules (through localized swelling in the interlayer region).
2. Thermodynamic frustration can be alleviated by adding molecules, changing the overall chemistry and preferred state of the region.
3. Strong interactions between self-fabricating blocks preclude incorporation of additional molecules.
4. Interactions and properties designed into the endblocks promote localization of an added molecule (solute) into the interlayer region.

Designed interactions can include acid endblocks to attract and localize basic solutes, low amino acid volumes in the endblocks to attract solute molecules that balance the interlayer volume and density, matched endblock-solute hydrophobic/hydrophilic interactions. It is important to note (and a key feature) that the "solute localizing" properties designed for the end blocks need not be entirely enthalpic (chemical interactions) in nature, but can include entropy-based design ideas as well (volume, molecule shape, flexibility).

Molecules absorbed into these designed materials (from designed molecules) will interact with a densely packed "brush" of end blocks, and the strength and nature of this interaction will determine whether a solute molecule can enter the material and diffuse into the material interior. If the endblocks are chiral, a chiral interaction occurs between solute and the nanobrush within the material for every few Angstroms of diffusion. Even non-specific interactions are expected to be chirally selective for diffusion of enantiomers through the brush. The extremely large surface area provided by the brush for interactions provides high selectivity, the possibility of a largely entropy-driven designed diffusion and interaction process ensures that separation is not specific to a particular well matched solute-endblock pair.

Separation has been observed for a test chiral molecule in silk-like and collagen-like designed oligopeptides. Acid base interactions were used to localize the test molecules in the chain end regions. Two processes were used to absorb the test molecule into the material: co-self-assembly from solution and swelling of an assembled miniblock oligopeptide nanomaterial with a solution of the test molecule. Both processes result in chiral separation, but smectic or higher level order is required in the oligopeptide nanomaterial to achieve good results. Thus we can elucidate some key design features for chiral separation using these materials:

1. Robust smectic layer formation.
2. Functional blocks used to localize solute in interlayer region (enthalpiclly or entropically).
3. Chiral functional blocks forming nanoscale chiral pores or interlayer brushes to provide a high surface area of interaction.
4. Sufficient structure and density in the nanomaterial to prevent non-specific diffusion (smectic or higher order, density comparable to homopolymer or greater).
5. Chemical compatibility with solute and solvent for solute. Ideally the nanostructured material should swell in the solvent to promote solvent diffusion, but not dissolve. Swelling should be limited to <50% increase in the volume of the endblocks (e.g. if endblocks are 20% of the material a swelling of not more than 10%).

Chiral enantiomers can be separated by diffusing the racemate into the material in solution and then removing the material, rinsing it to remove "bad" enantiomer on the material surface, and solvent extracting the "good" enantiomer. Alternatively, the material could be used to "sponge" up the undesirable enantiomer leaving the desired enantiomer behind. As yet another possible separation process, the material could be made into a membrane which would allow only one enantiomer to pass through.

Materials can also be designed (at the molecular level) for less demanding applications than chiral separations. Simple achiral chemical selectivity can be incorporated for permselective membranes and separation beads. The designability of both molecules and materials also allows selection based on size, through design of the size of layer and sublayer features (>2 nm particles filtered), and through design of layer densities using mismatched monomer sizes in the oligomer blocks to create molecular scale porosity.

Other applications for a chirally separating material extend beyond chiral separations to include chiral catalysis, enzyme substrates, and other combined chemical separation and reaction processes. For example a chiral enzyme might experience enhanced chiral selectivity in a chiral environment due to chirally differentiated constraints on the diffusion and reorientation modes of reactants. Different activated states of reactants and different conformational states of a chiral catalyst would be expected to be preferentially stabilized in an environment with chiral physical features on the length scale of a molecule when compared to a more symmetric environment. At the surface of a chiral nanopatterned material, a loosely bound enzyme (for example tethered to a swollen hydrophilic nanolayer by a single covalent bond) would experience an environment which has features of homogeneous catalysis. The enzyme would be surrounded by an essentially fluid "gel" where a sharp symmetry breaking solid surface is not defined. sorption to a solid surface) nor constrains the geometry of reactant approach. However, the enzyme would nevertheless be bound to the material and recoverable. Furthermore the fluid (of solubilizing ends or blocks) surrounding the enzyme would be densely packed and chiral, encouraging chiral interactions to stabilize different enzyme conformations (when compared to a symmetric environment).

Along similar lines a chiral catalyst for a polymerization could be embedded in the chiral nanomaterial membrane. Chirally biased transport of monomers and stabilization of a preferred chirality (for monomers that readily racemize) could be used to direct catalysis and subsequent regularity/purity or the product polymer or other reaction product.

Samples

A set of samples have been prepared from concentrated solutions of natural silk using a solvent templating technique. These samples initially formed as hydrogels which grew from a solvent interface into the aqueous silk phase. These hydrogels lose more than 90% of their volume on drying. Comparisons of dried gels prepared using chloroform as the templating solvent to dried gels prepared using amyl alcohol have been made. In X-ray studies (WAXS), the gels prepared using chloroform are oriented biaxially whereas the amyl alcohol gels have a weak uniaxial orientation. Orders of a 100-110 Angstrom layer spacing as faint blips on top of the WAXS pattern are also observed. The layer spacing in synchrotron SAXS has not been reproduced, but at this time it is not known whether the low angle spacing is imaginary (an artifact of the detector design) or whether its absence is due to a combination of low exposure times in the synchrotron beam, sample orientation and large oriented domain sizes, and the one dimensional detector at the beam line. Small features (very regular) of the same size are observed in FESEM.

FTIR data on either film was not able to be obtained at this time. In transmission and reflection IR experiments, most of the raw signal required to obtain a spectrum (a difference spectrum between raw signal and background) is lost. This spectral dropout occurs in the wavelength region from 2 and 8 microns. In ATR one does not see any spectrum or any significant raw signal using ZnSe as the ATR crystal. Since ATR should allow one to see any material that is really there, and ATR from similarly problematic films have been obtained when a Si cell was used, we speculate that the films strongly polarize infrared radiation in this wavelength region. The ZnSe crystal used is a hexagonal, randomly oriented material and is thus optically anisotropic—it induces a polarization state in the incident infrared radiation. Silicon is cubic and is optically isotropic. In addition to polarizing the infrared radiation, the samples have no spectrum in diffuse reflectance IR (thus ruling out Bragg diffraction), indicating that they behave as completely IR absorptive little black bodies even when ground into a fine powder. The grain size of the powder (a few microns) can be used to place an upper limit on the smallest film thickness required to obtain a protein black body in the infrared. This may correspond to one full cycle of some chiral feature in the films, but it is also possible that a partial feature has the same effect. This is similar to a related phenomenon where dense clusters in an inhomogeneous material preferentially absorb infrared radiation, resulting in a lower total signal for the material in the clusters, and spectral information weighted towards the less dense material. This phenomenon is relevant to the difference spectra; we are seeing anomalies in the raw spectra.

Since the structures are all reasonable in terms of chiral liquid crystalline and polymer phase behavior and microstructure, the observed phenomena are not specific to proteins but can be generalized to any molecule type, provided that it can be designed to form the appropriate shapes. So as discotic liquid crystalline phases and order are common to all disc shapes molecules, the structures may be general to all polymers which can form chiral hairpins and folded structures. Different molecule types may give better materials properties and also allow one to pump up the strength of the relevant chiral interactions and produce even twistier materials (with analogous morphologies).

The native silk films are comprised of wavy, probably interconnected, layers. FIGS. 1-8 depict SEM images of differently oriented fracture surfaces, where the edges of the wavy layers can be seen. In other orientations the morphology looks like a honeycomb of ~75 nm features. Some ~11 nm pores in a very regular honeycomb inside the 75 nm features can be made out. These may be responsible for the bizarre infrared behavior observed. The materials show marked differences in surface morphology (as well as orientation) depending on templating solvent. There may also be small differences in the phantom layer spacing. The less ordered amyl alcohol film is a very good ion scavenger. The chloroform templated film scavenges chiral ions. Both films will soak up enough rare earth salt to become refractive and shiny.

All of the native silk materials will swell very slightly and soften in water or weak acid, and will scavenge bases and become hard. They are insoluble in alcohol. They are thermally stable to 290° C. at which point they degrade rapidly without melting. They appear to be fairly tough and hard, and the starting materials and processes are relatively inexpensive.

Fibrous-Protein Peptide-Based Smectic Gels

Biologically inspired nanopatterned materials have been designed, synthesized (as complex molecules) and fabricated. These materials have some unusual spectral features in the mid-far infrared. They can be fabricated efficiently, combined with inorganics and salts to create nanocomposites (to modify specific properties), fabricated from molecules which can be synthesized in quantity, and have reasonable mechanical and thermal properties. The materials incorporate a repetitive nanoscale pattern of chemistry and molecular orientation which persists to macroscopic length scales (in some cases millimeters or centimeters in initial studies). The current focus is on nanoscale material patterns which incorporate a small nanoscale multilayered structure which is achieved through molecular design and self-assembly, but other types of geometric nanoscale patterns are observed and fabricated as well. Engineering of all of the geometric features (and many chemical features) of the nanoscale pattern is possible through molecular level design.

The materials are peptide-based, and several distinct classes of polypeptides and oligopeptides have been defined which are loosely based on natural fibrous proteins such as collagens, keratins, and silks. The individual oligopeptides within each class incorporate simplified versions of patterned amino acid motifs found in each protein type (collagen, keratin, silk) with designed variations included to enable study of very specific molecular level influences on folding, material self-assembly, and resulting materials properties. A strong interest in the design of these oligopeptides has been the creation of model molecules that allow us to utilize liquid crystalline behavior in designing simple robust approaches to chemical and physical patterning of materials at the micro- and nano-scales. A key feature of this approach as mentioned previously includes designing molecular materials which segregate to form nanoscale long-range ordered patterns as a thermodynamically favorable state, often through built-in molecular chemical complexity resulting in thermodynamic "frustration". A major avenue being studied to form materials from these molecules is manipulation of a folding or aggregation transition which allows the molecule to change it's liquid crystalline self-assembly behavior from flexible soap-like lyotropic liquid crystallinity to chiral oriented rigid rod thermotropic liquid crystalline behavior. Our ability to manipulate the transition from one type of behavior to the other gives us significant control over macroscopic features of the material such as domain size, precipitate shape, etc.

While the materials obtained are biopolymeric in origin, they are not traditional "folded proteins", but act much more like synthetic nylons (proteins are very fancy nylons in their chemical backbone structure). They do not form compact natured globules. Instead interactions between molecules are favored, resulting in a molecular solid with reasonable thermal stability, toughness, and strength. Qualitative tests of mechanical properties indicate that they behave like "good plastics", having properties similar to nylons. Preliminary thermal analysis in an X-ray beam line suggest that structure is retained to approximately 200° C. for the materials tested thus far. In one of the classes of materials optical clarity and optical orientation (a birefringent pattern) were observed to persist to 170° C. Variants have been designed with different solubility behavior, and thus considerable control over chemical processability and chemical resistance has been achieved as well.

Unlike many structural biopolymers and experimental high performance polymers such as block copolymers, the amino acid sequence and size range of our oligopeptides allows facile biosynthesis and scale up. Initial attempts at Biosynthesis have already resulted in high yields and scale up routes for the most interesting sequences are being actively pursued. The intermediate size of the molecules—too small to be "polymers" but too large to be "small molecules"— provides advantages in both synthesis and processing. The molecules are small by protein standards, and thus biosynthesis and scale-up do not present an insurmountable technical challenge (compare this to the long history of attempts to biosynthesize high molecular weight collagens and silks). Solubilization of the molecules during purification and processing is also simplified by their relatively low (for a protein or polymer) molecular weight. They are large molecules when considered as thermotropic liquid crystals, and their size helps to stabilize liquid crystalline textures while solvent is removed, resulting in liquid crystalline ordered solids. The chemical complexity of the molecules can be designed and exploited, allowing each individual sequence to adopt different chemically distinct "states" (which are induced). This ability to induce a molecule to change it's shape and chemical properties allows one to engineer irreversible solubility changes into the molecules, making stable materials from processable (under mild conditions) molecules.

Figure 9:
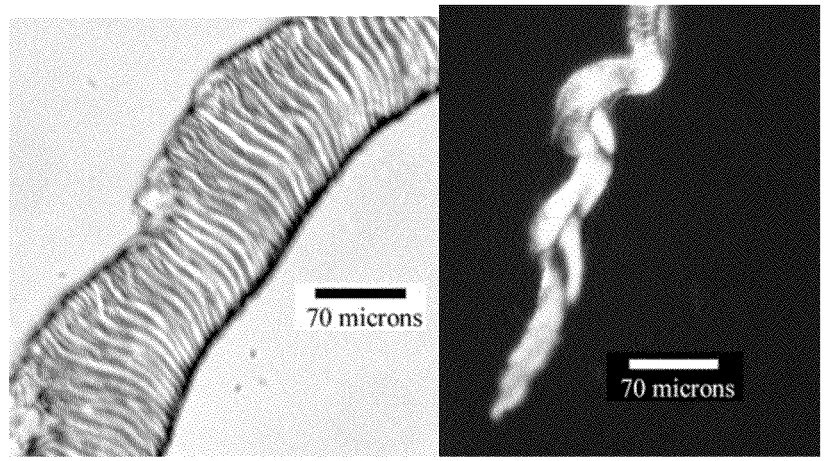
FIG. 9 depicts self-fabricated textured "tapes" from a peptide with sequence $(Glu)_5(Ser-Gly-Ala-Gly-Val-Gly-Arg-Gly-Asp-Gly-Ser-GlyVal-Gly-Leu-Gly-Ser-Gly-Asn-Gly)_2(Glu)_5$. 1. Optical micrograph shows a ~10-15 micron texture which persists through the material thickness. The material is optically transparent. 2. Polarizing optical microscopy reveals patterned birefringence, indicating that the topographic texture is due to a changing material orientation. 3. SEM image shows the topographic structure of the tape. The difference in periodicity observed in SEM and optical microscopy is due to the fact that top surface and bottom surface ridges are both observed in the optical image (resulting in an apparently shorter period).
Figure 9:
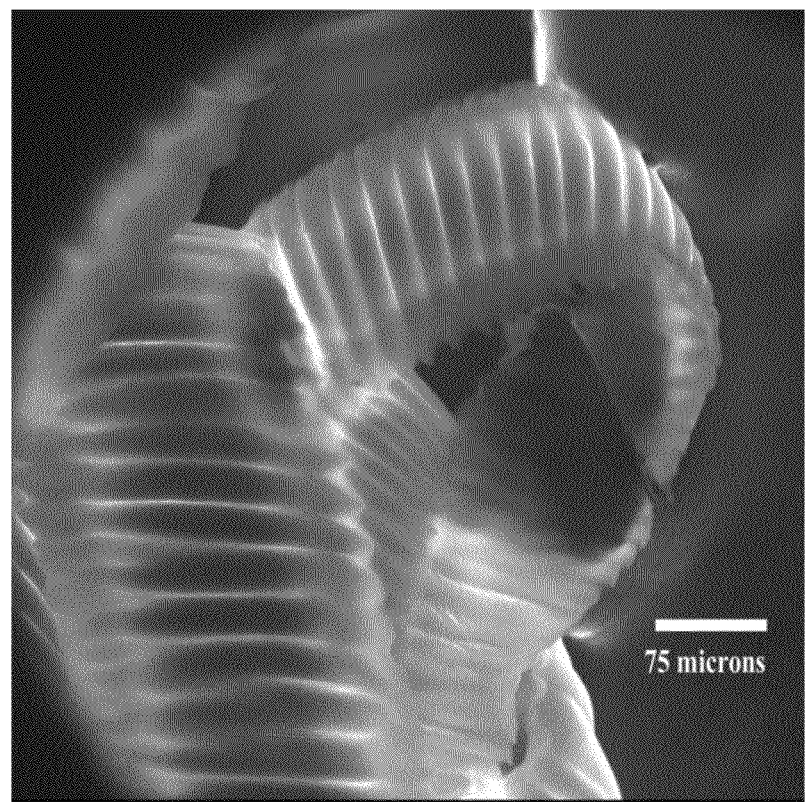
Figure 10:
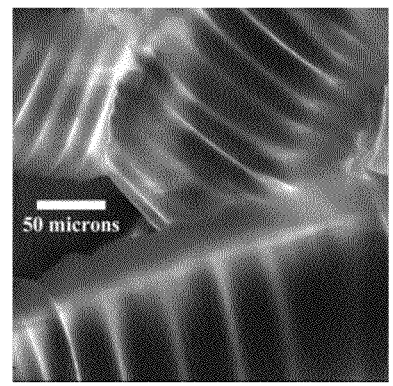
FIG. 10 depicts self-fabricated tapes of $(Glu)_5(Ser-Gly-Ala-Gly-Val-Gly-Arg-Gly-Asp-Gly-Ser-GlyVal-Gly-Leu-Gly-Ser-Gly-Asn-Gly)_2(Glu)_5$ have "patterns within patterns" or a long-range ordered structure consisting of hierarchical nanoscale to microscale patterns; 1: the self-limited width and thickness of the fibers (~120 microns, 50 microns respectively) form the largest length scale in the hierarchy; a 40 micron periodic texture is observed running along the tape; 2: within the ridges of the 40 micron texture a 3 micron subtexture is observed; 3: a submicron texture of inclined sheets or layers can be observed (<40 nm, but exact size is below the resolution of the scanning electron microscope); TEM studies indicate a layer spacing of 5 nm.
Figure 10:
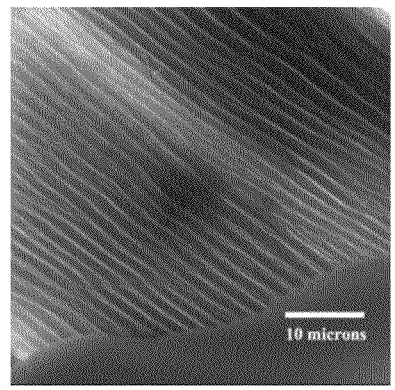
Figure 10:
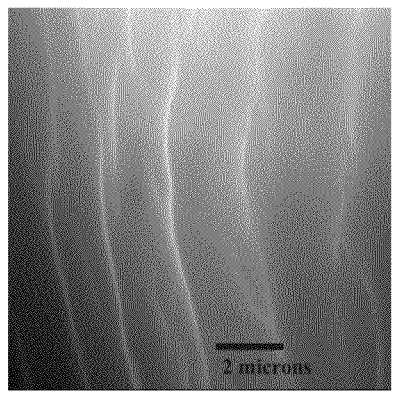
Figure 11:
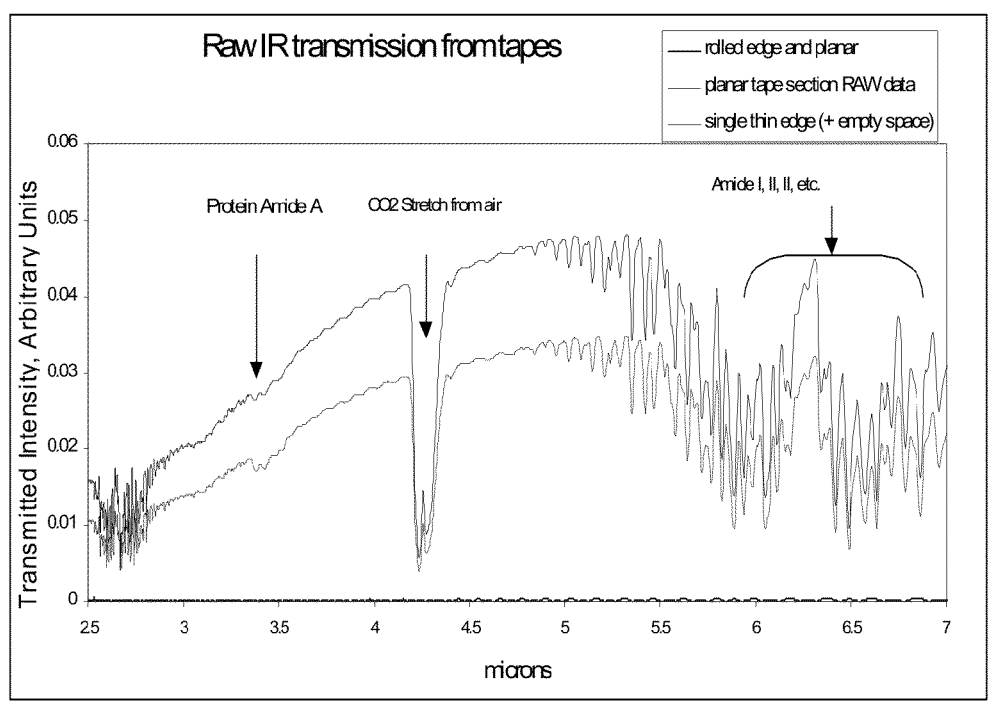
FIG. 11 depicts an IR spectra of self-fabricated tapes of $(Glu)_5(Ser-Gly-Ala-Gly-Val-Gly-Arg-Gly-Asp-Gly-Ser-GlyVal-Gly-Leu-Gly-Ser-Gly-Asn-Gly)_2(Glu)_5$. Typically IR spectra for molecules are seen as very small differences in IR transmission relative to a large backround, which must be subtracted out. Raw data (no background subtraction) is shown for transmission FTIR spectra through different regions (orientations) of the tape structure. Two orientations show very typical protein absorbance spectra over a high background. However in some orientations the IR radiation does not reach the detector.

Many of the molecules under study exhibit a number of chiral smectic (nanolayered) liquid crystalline phases, which can be dried under controlled conditions to create nanolayered materials. An example is the textured oriented "tape" shown in FIG. 9 (silk-like). These materials also posses a hierarchy of patterned features at different length-scales, which may be responsible for some of their optical behavior. This hierarchical order or patterning is shown in FIG. 10 for the textured tape. A number of these nanolayered materials have been studied, and a common feature for both collagen-like and silk-like materials is the loss of part of the raw mid-IR spectrum when FTIR spectra are obtained from the materials in a spectrometer. The effect is orientation dependent for many of the materials. In FIG. 11 a set of transmission spectra are shown. The raw background has the highest intensity. Very thin tape regions in an orientation that does not have an abnormal affect on IR spectra produce very ordinary protein or peptide IR spectra. In certain orientations we see spectra such as the one represented in FIG. 11.

Figure 12:
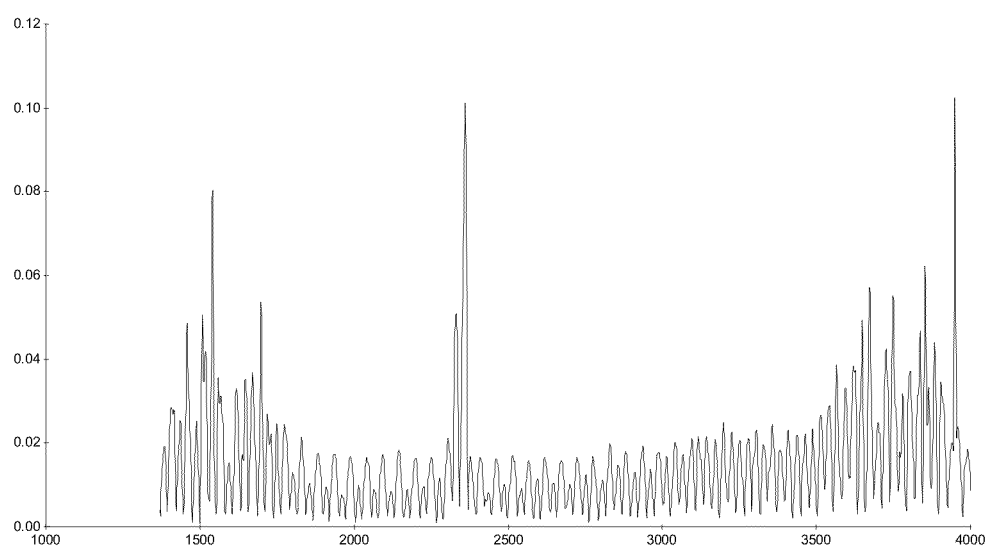
FIG. 12 depicts an IR spectrum modified by tape with scale expanded to show spectral features. Instead of an absorption or transmission spectrum, a pattern of 2 overlaid sinusoids (one has a 50/cm period, the other a 25/cm period. The effect for this material appears strongest in the 1750-3500 $cm^{-1}$, or 5.7-2.9 micron range.

The regions of the infrared which are strongly affected (the wavelengths) have been correlated to the periodicity of materials morphology patterns for one of the classes of oligopeptide materials (collagen-like). Different processing conditions used to make the (silk-like) tapes, used as an example here, also result in different periodicities in their morphological texture and in differences in the infrared wavelength regions affected. There is not enough data on all samples producing the effect to develop clear correlations between processing, morphological texture, and infrared behavior for all of the materials which possess unusual infrared behavior. However, it is believed that these correlations exist. Because very normal protein absorption spectra can also be obtained from very specific orientations of the nanolayered materials, or through grinding of the material to reduce the presence and persistence of long range order, the infrared absorption behavior of these substances is unremarkable at the molecular level. However the presence of a long-range ordered pattern of molecular orientations in the self-assembled materials is causing the infrared radiation to miss the spectrometer detector and perhaps go somewhere else. Because all of the observable materials textures are due to changes in the local molecular orientation or the orientation of nanoscale layers in the structure, periodic physical features should also correspond to periodic modulations in the refractive index of the material. The raw spectra in the strongly affected regions have a strong sinusoidal character, as can be seen in the rescaled data in FIG. 12 (unfortunately, due to rescaling the Y-axis intensities are no longer physically meaningful). In many instances these sinusoidal patterns are attenuated or "chirped" in the small wavenumber/long wavelength part of the spectrum. If these materials can redirect or guide radiation in the mid-far infrared wavelength region, they may be quite useful in redirecting infrared signatures either to a heat sink, or a detector, or a spectrometer for in-line chemical analysis.

Figure 13:
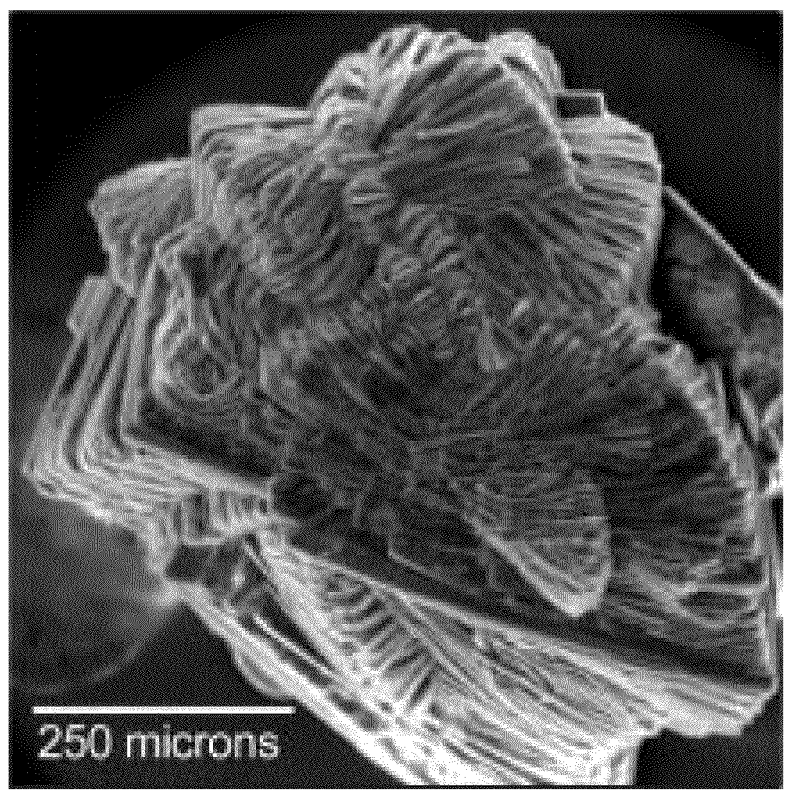
FIG. 13 depicts twisted polycrystals obtained by salt precipitation of an oligopeptide with Na-EDTA.
Figure 14:
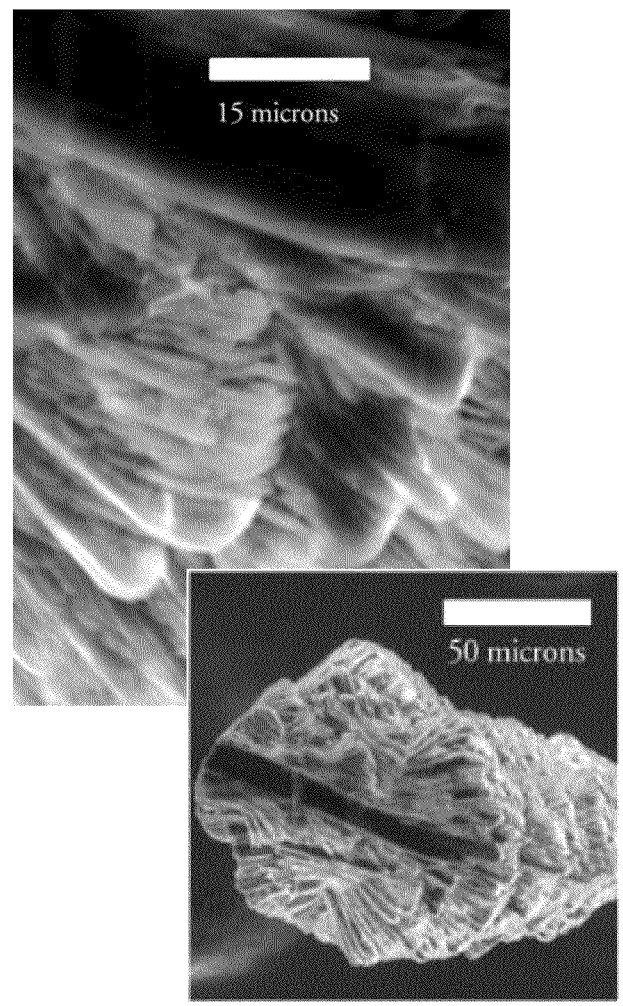
FIG. 14 depicts ordered "corkscrew" polycrystalline oligopeptide salt precipitate as a hierarchy of twisted ordered structures.
Figure 15:
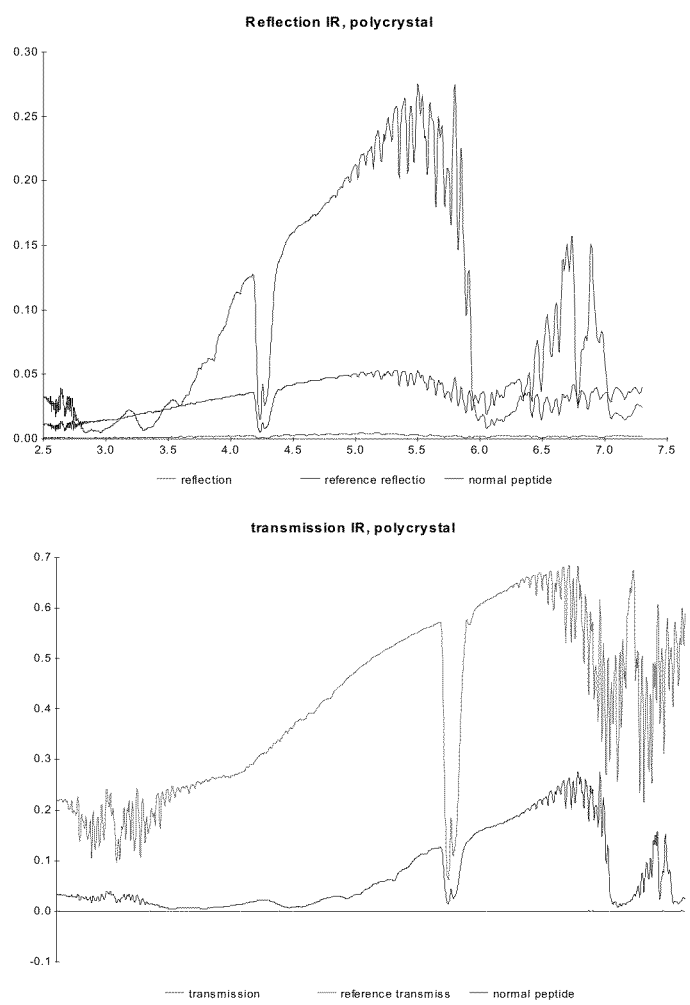
FIG. 15 depicts reflection and transmission FTIR spectra for ordered polycystals. TOP: reflection infrared spectrum, Raw data. A glassy disordered material of the oligopeptide is more reflective than the background. An ordered periodic nanolayered material from the same peptide is shown, and clearly reflects far less of the infrared radiation. BOTTOM: transmission spectra for background, unordered peptide material and a chemically identical nanolayered ordered material of the peptide. Spectrum is greatly attenuated for the ordered material.

This effect is also observed in layered polycrystals of the same oligopeptides (collagen-like and silk-like classes) cocrystallized with an organic salt (FIG. 13). These layered polycrystals have individual lathe shaped crystallites arranged in regularly twisting structures (FIG. 14). In this case the infrared effect appears most pronounced for the most highly organized and regular twisted polycrystalline materials. Attenuation is observed in both reflection infrared spectroscopy and transmission infrared spectroscopy (FIG. 15). The ordered material is thus both less transmissive and less reflective than the ZnS background in the affected region of the infrared. SAXS data indicate a strong nanoscale layered periodicity (preliminary and unprocessed, not shown). Thermal studies using WAXS and SAXS indicate a slightly lower thermal stability for these salted polycrystalline materials, around 160° C., when compared to pure oligopeptide materials. Very local phase changes occur at fairly low temperatures (<100° C.). These local changes can be attributed to extension of the molecules in the nanoscale layers, resulting in a change in layer spacing. Such local phase changes may provide useful avenues for manipulating the properties of the materials, but have not been studied in detail yet. The polycrystals are qualitaitively "hard" (as compared to other polymeric crystals) and difficult to grind (tough). The relatively low thermal stability of these polycrystals may be due to the choice of salt—in this case a low melting organic molecule. Other salts have produced nanocomposites which retain the nanolayered structure imposed by the oligopeptides, but which appear to be more thermally stable than pure peptide, although this data is very preliminary.

The oligopeptide materials can be processed into tough precipitated tapes, polycrystalline aggregates, or thin films (poorer mechanical properties, but we're addressing this). All of these materials manipulate the infrared spectra although the silk-like class of materials appear to affect a broader band of the spectrum than the collagen-like materials. The collagen-like materials affect the 3-10 micron region of the infrared most strongly, and have material periodicities in the same size range which appear correlated to the spectral band affected. These materials features can be manipulated through selection of sequence patterns in the chemical structure of the molecules, through tuning of the anchoring behavior of the molecules in the liquid crystalline state during processing, and are expected to also respond to a low voltage electrical field applied during formation of the liquid crystal and drying to form a solid material. Control of material texture variations and their correlation to infrared spectral behavior has not yet been systematically addressed for the silk-like class of biopolymer materials (tapes and polycrystals in the examples). However differences are observed depending on the solvent conditions used to create the tapes, and differences in the region of the infrared affected are also observed.

EXEMPLIFICATION

Example 1

Preparation of Silk

Materials—Cocoons of *B. mori* silkworm silk were kindly supplied by M Tsukada, Institute of Sericulture, Tsukuba, Japan. Chloroform, hexane and iso-amyl alcohol were purchased from Aldrich and Fisher Scientific and used without further purification. Tris(2,2'-bipyridyl)dichlororuthenium (II) hexahydrate ("Rubipy") was purchased from Aldrich.

Preparation of Regenerated *B. mori* Silk Fibroin Solutions—The silk fibroin solutions were prepared by either one of two methods: Method A—for preparation of bulk solids—*B. mori* silk fibroin solutions were prepared as follows. Cocoons were boiled for 30 min in an aqueous solution of 0.02 M $Na_2CO_3$, then rinsed thoroughly with water to extract the glue-like sericin proteins. The extracted silk was then dissolved in 9.3 M LiBr solution at room temperature yielding a 20 wt % solution. This solution was dialyzed in water using Slide-a-Lyzer dialysis cassettes (Pierce, MWCO 2000) for 48 hrs. The final concentration of aqueous silk solution was 8.0 wt %, which was determined by weighing the remaining solid after drying. Millipore purified water, 17 MΩ, was used throughout all processing. No buffers, acids, or salts were added in final solution; Method B—for preparation of thin films—*Bombyx mori* silk cocoons were degummed using repeated washings in boiling water, sodium dodecyl sulfate (SDS) and $NaCO_3$ to remove the sericin, leaving pure fibroin. For the first washing 6.5 SDS and 1.0% $NaCO_3$ were used in boiling water. The cocoons were then rinsed with 0.4% NaCO3 in boiling water, and subsequently rinsed with boiling water alone. Other cocoons were degummed without SDS, using only $NaCO_3$ and boiling water. Amino acid analysis has been used to assess the protein composition of fibroin prepared in this manner and no sericin was detected. Valluzzi, R.; Gido, S. P. *Biopolymers* 1997, 42, 705-717; Valluzzi, R.; Gido, S.; Zhang, W.; Muller, W.; Kaplan, D. *Macromolecules* 1996, 29, 8606-8614. The degummed fibroin was rinsed thoroughly with distilled water and dissolved in a 9.1 M solution of LiSCN in water. In order to remove the salt, the fibroin and LiSCN solution was then dialyzed against frequent changes of distilled water for several days. The dialyzed fibroin solutions were filtered using a 100 μm syringe filter to remove dust and any protein precipitate.

Example 2

Preparation of Smectic Gels

Preparation of interfacial gels—Aqueous-chloroform, -hexane and -iso-amyl alcohol interfaces were prepared by adding silk peptide solution into glass vials containing each solvent. The vials were then capped to prevent evaporation and left at room temperature overnight. The resulting interfacial gels were collected and dried at room temperature overnight.

Desalted, HPLC purified, and lyophilized collagen-like peptide was obtained from the Protein Chemistry Core Facility at the Tufts Medical School. The sequence was $(Glu)_5(Gly\text{-}Val\text{-}Pro\text{-}Gly\text{-}Pro\text{-}Pro)_6(Glu)_5$. The glutamic acid blocks were added to the ends of the peptides to promote solubility in water so that contaminant salts would not complicate analysis. Similar peptide design strategies have been used by Rotwarf et. al. to examine the solution behavior of β-sheet forming peptides. Rotwarf, D. M.; Davenport, V. G.; Shi, P.-T.; Peng, J.-L.; Sheraga, H. A. *Biopolymers* 1996, 39, 531-536. The collagen-like peptide was dissolved in 18 MQ Millipore filtered water at a concentration of 1 mg/ml peptide in water. No salt or acid or extra reagent was required to aid dissolution. The solution was allowed to stand in an air-tight capped vial overnight, and then a gold mesh TEM grid (no substrate film) was dipped through the air-water interface.

Example 3

Characterization

Figure 16:
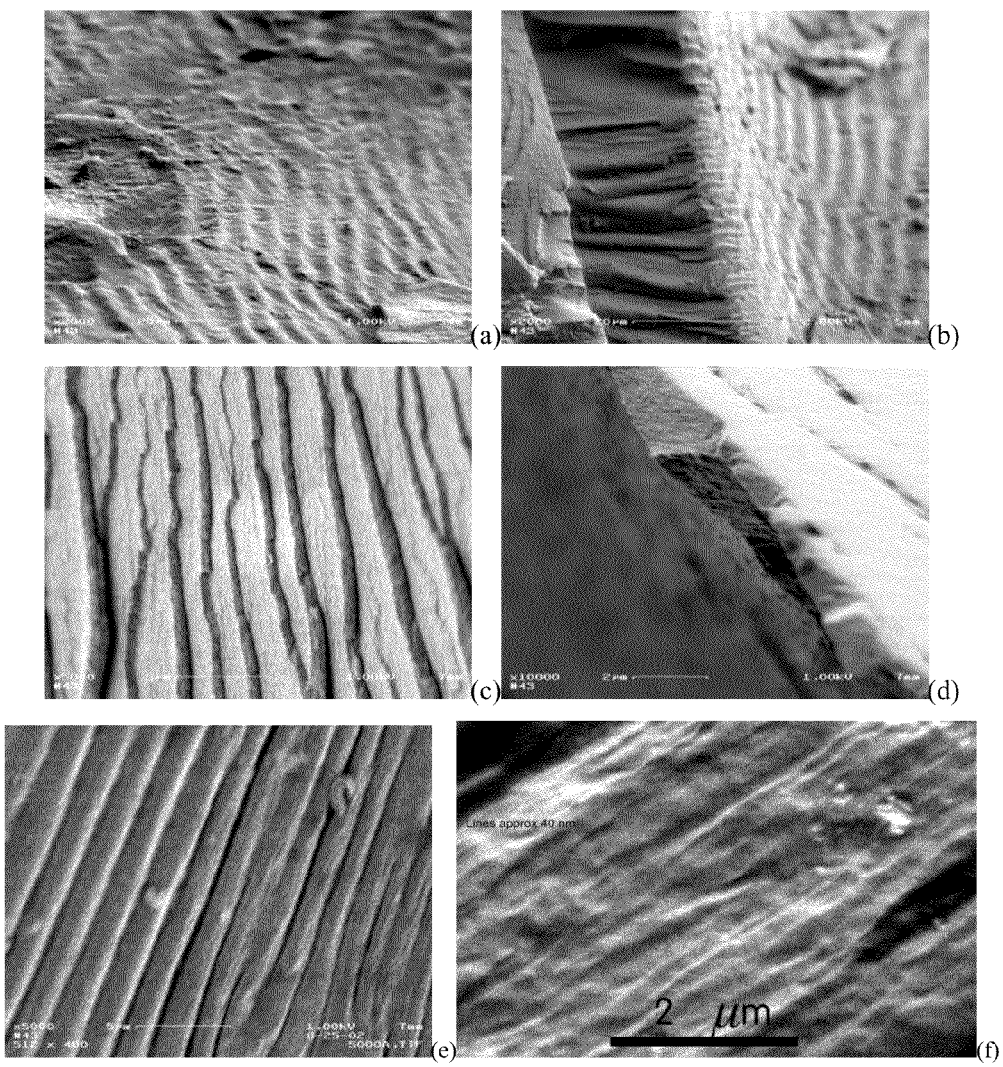
FIG. 16 depicts ordered textured surfaces and interiors from templated gels (a) chloroform templated gels have a wavy surface texture covering the surfaces which were in contact with water; (b) a fracture surface from the chloroform templated gel reveals a "skin" of the wavy pattern, which forms channels down into the interior; the interior has a different structure, which appears to be made of wavy plates; (c) templated surface of amyl alcohol templated material (in contact with water); (d) higher magnification image of the edge of the region in c, showing a "skin" core structure and a patterned texture throughout the material; (e,f) amyl alcohol dried film after swelling in an aqueous solution of ruthenium compound and extraction of ruthenium compound by swelling in water; (e) wavy lines indicate reorientation of ordered structures within the material; (f) at high magnification (20, 000 ×) lines 38 nm in width are observed.
Figure 17:
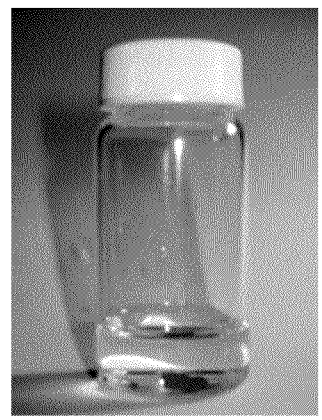
FIG. 17 depicts amyl alcohol templated gel after soaking in Aqueous Tris(2,2'-bipyridyl) dichloro ruthenium(II) hexahydrate ("Rubipy") solution for 1 day. Much of the Rubipy has migrated from the solution into the silk gel. Initial migration is rapid and chirally selective (occurs over roughly 1 hour). Additional migration occurs slowly after this for roughly 1 day and is less chirally selective. Chloroform templated gels do not exhibit complex diffusion behavior and are chirally selective throughout the swelling process.
Figure 18:
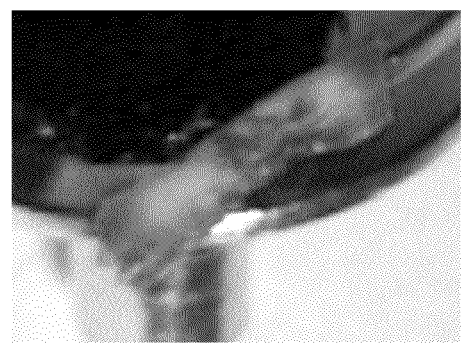
FIG. 18 depicts a cross section of amyl alcohol templated gel after swelling in Rubipy for 1 hour. The Rubipy penetrated rapidly into the outer "skin" layers of the gel (bright orange), and more slowly into the interior (yellowish region).

Characterization—Gels treated with ruthenium compound were cut to obtain cross sections. The amyl alcohol gel in Rubipy is shown in FIG. 16. The ruthenium compound (Rubipy) has an orange color, and is in the silk gel in a higher concentration (bright red orange) than in the surrounding solution (light yellow orange). Gels treated with Rubipy for 1 hour were sliced open to obtain cross sections (FIG. 17). These cross sections allow us to compare the structure of the gel with a lot of Rubipy absorbed to the structure of the interior, which has a lower concentration of Rubipy. A cross section is shown in FIG. 18, and a dark red-orange Rubipy-rich skin can be seen surrounding a clear yellowish silk core. Understanding and engineering the skin core morphology formed through the templating process is important for controlling the characteristics and function of the gels.

SEM—Images of dried gels were obtained with a LEO Gemini 982 Field Emission Gun SEM. Working distance was 7 mm and applied voltage was 1 to 2 kV. All images of gels were taken without any conductive coating. (FIG. 18).

Figure 19:
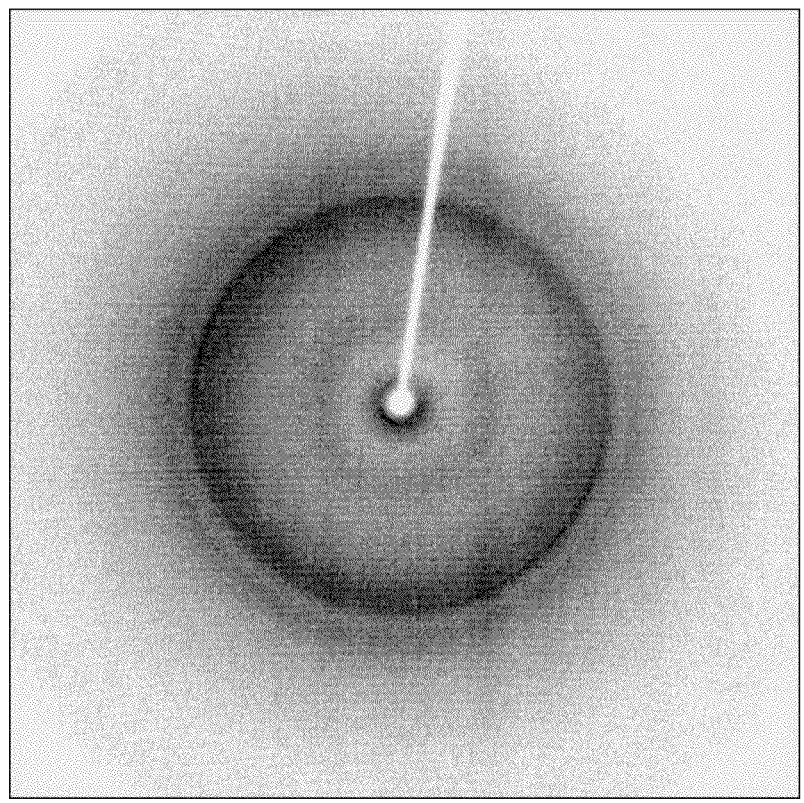
FIG. 19 depicts an X-ray diffraction pattern from chloroform templated gel. Dark arcs along the diffraction rings (arrow) indicate orientation.
Figure 20:
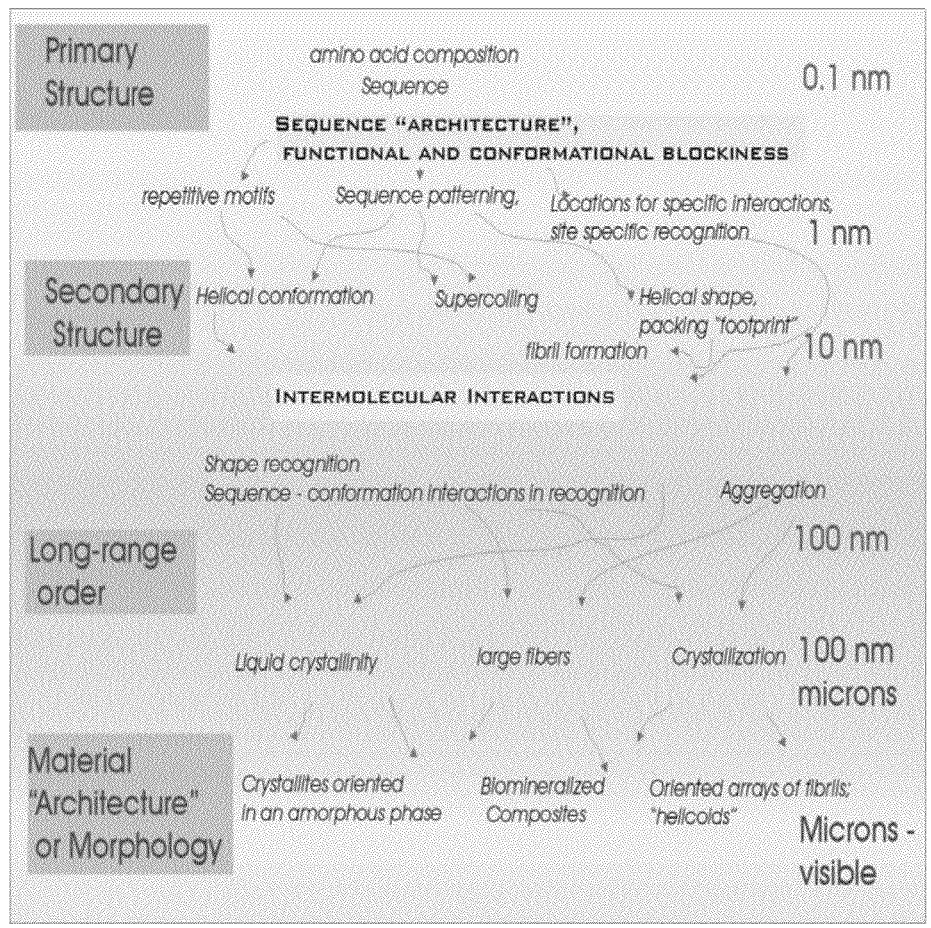
FIG. 20 depicts the non-globular nature of fibrous proteins.
Figure 21:
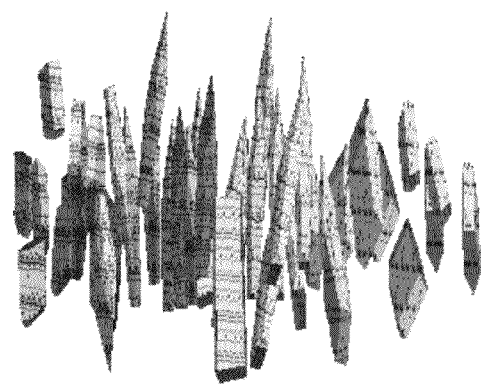
FIG. 21 depicts the long range order of liquid crystals.
Figure 21:
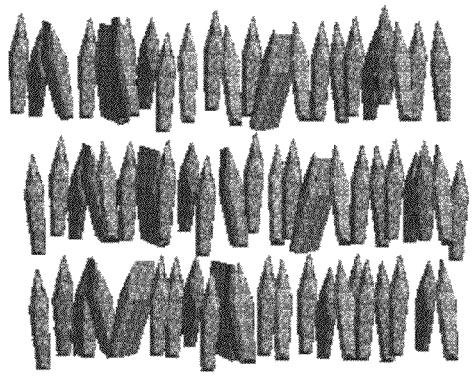
Figure 21:
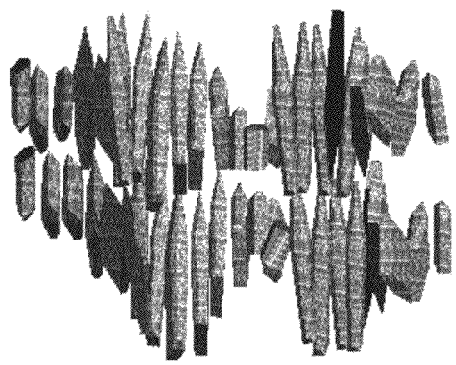
Figure 22:
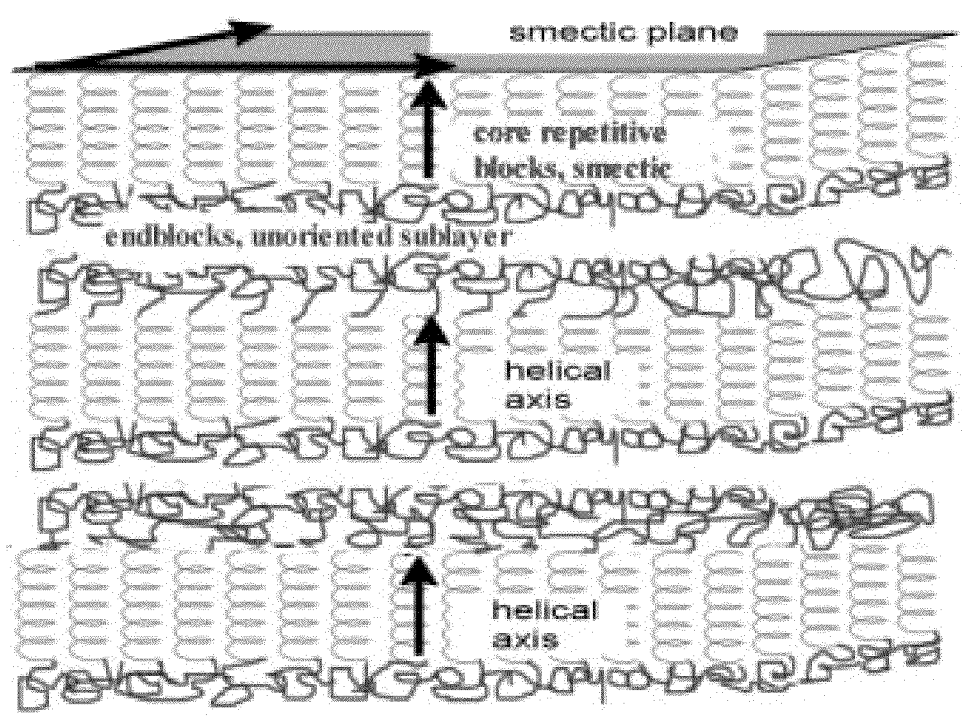
FIG. 22 depicts "frustration" in nanolayered crystals.
Figure 23:
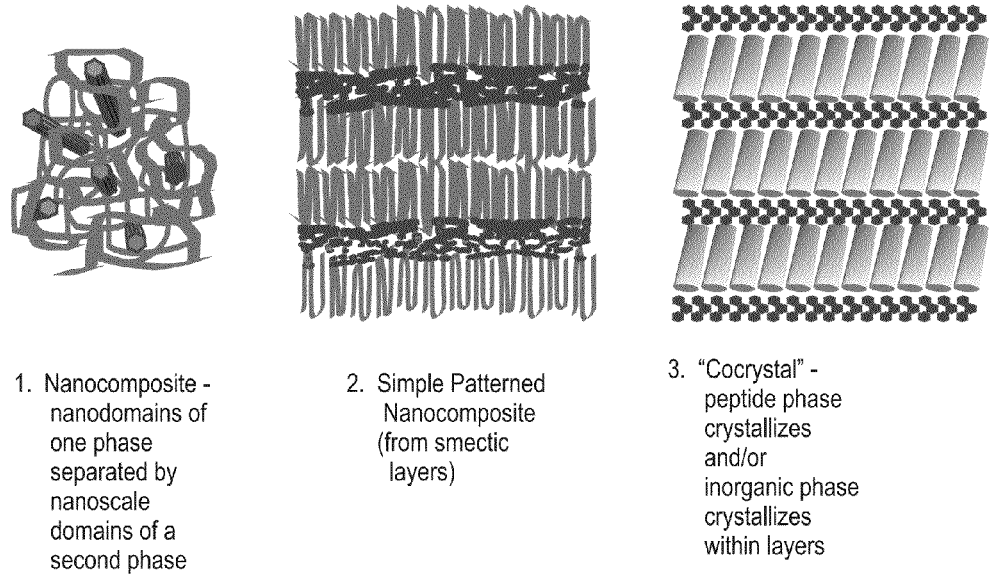
FIG. 23 depicts nanocomposites.
Figure 24:
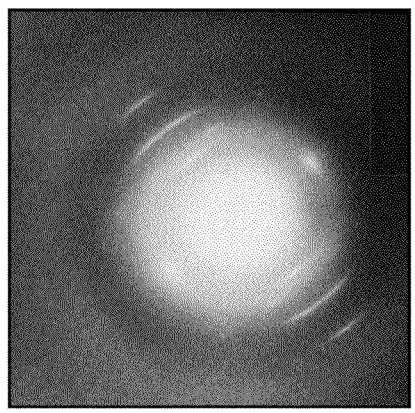
FIG. 24 depicts banded structures from native silk.
Figure 24:
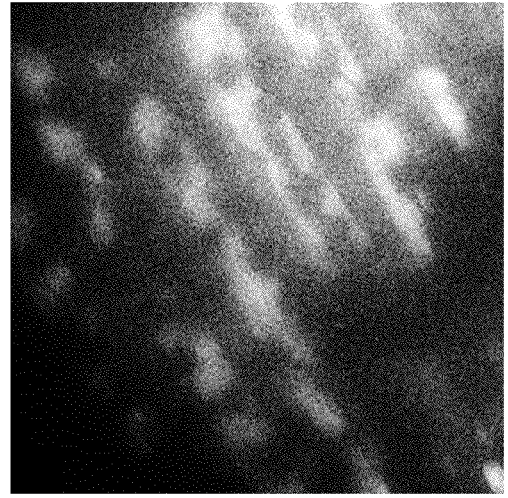
Figure 24:
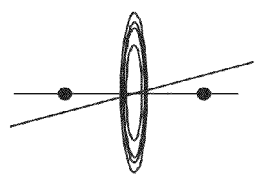
Figure 24:
Figure 24:
Figure 25:
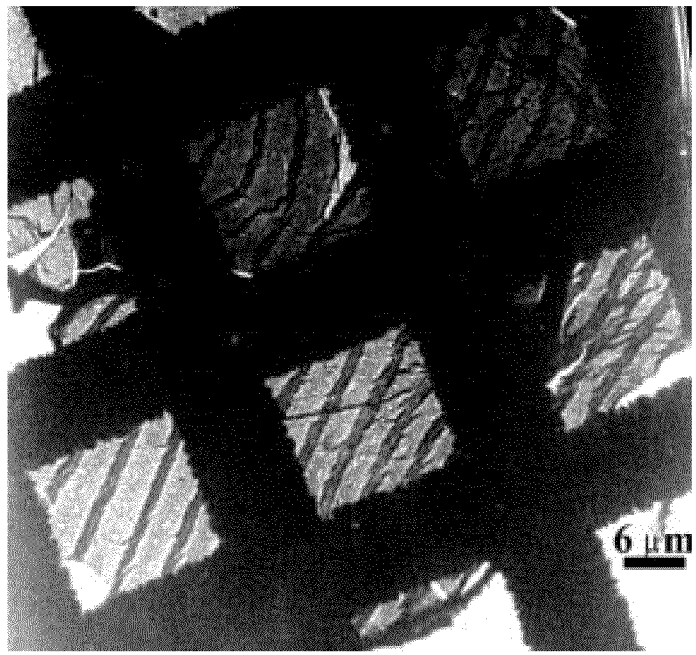
FIG. 25 depicts banded structures from engineered protein designed peptide.
Figure 25:
Figure 26:
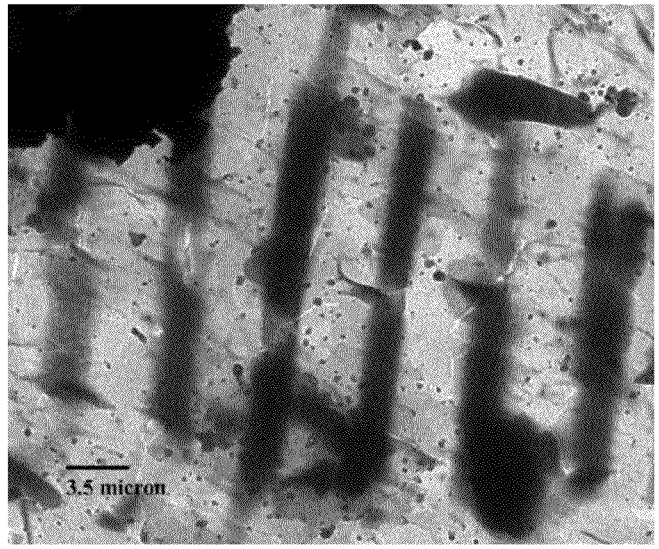
FIG. 26 depicts how hairpin structures allow silk liquid crystallinity.
Figure 26:
Figure 26:
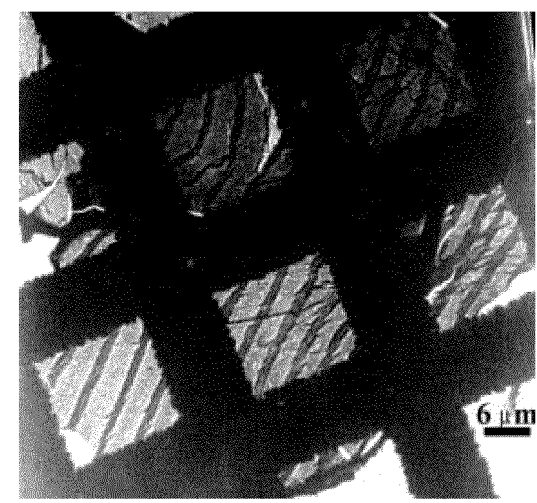
Figure 26:
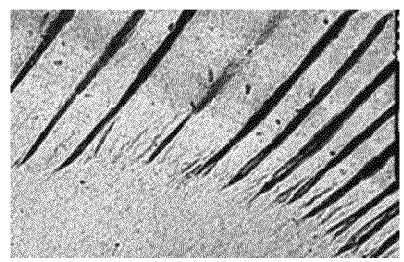
Figure 27:
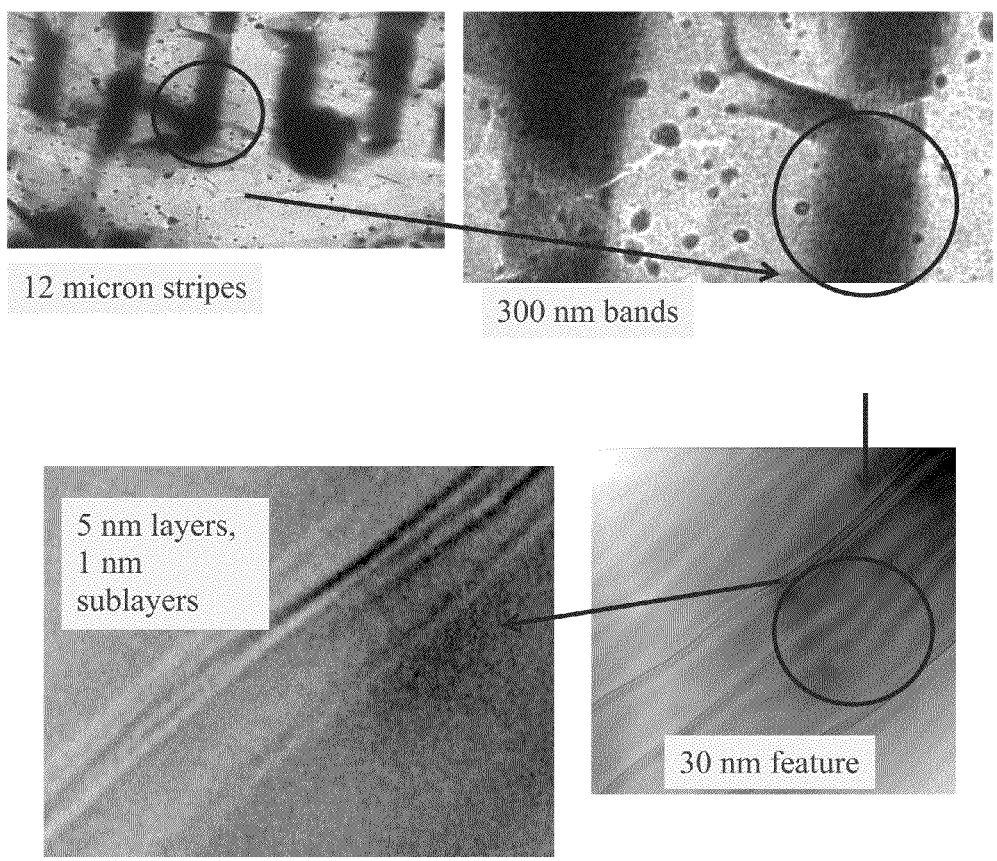
FIG. 27 depicts spider silk modification.
Figure 28:
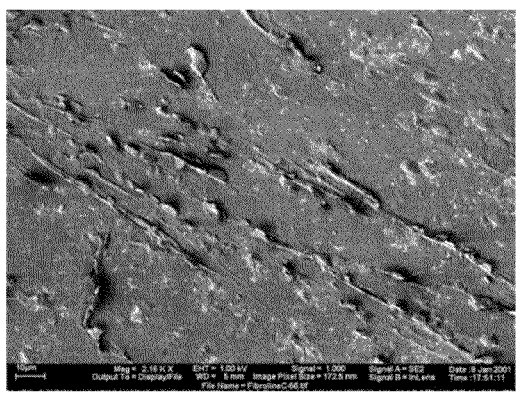
FIG. 28 depicts amphiphilic spider silk motif
Figure 28:
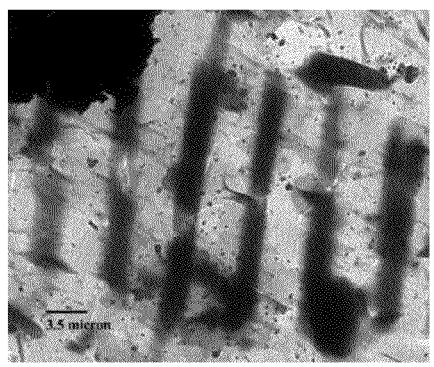
Figure 28:
Figure 29:
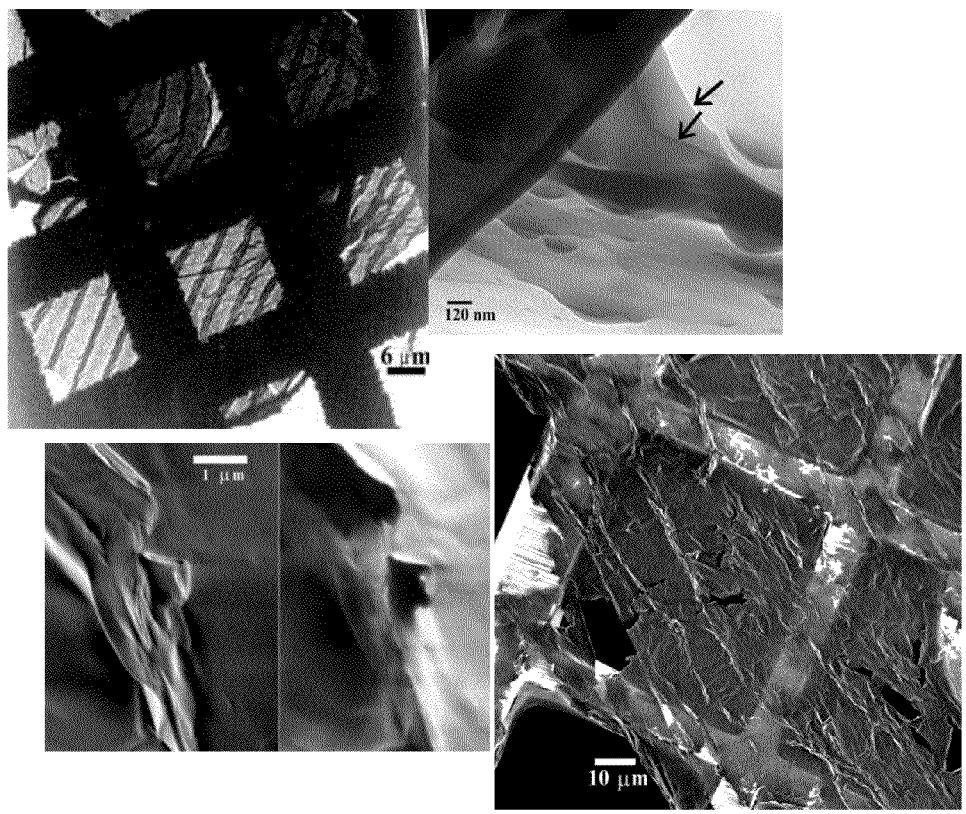
FIG. 29 depicts silkworm silk peptide models.
Figure 30:
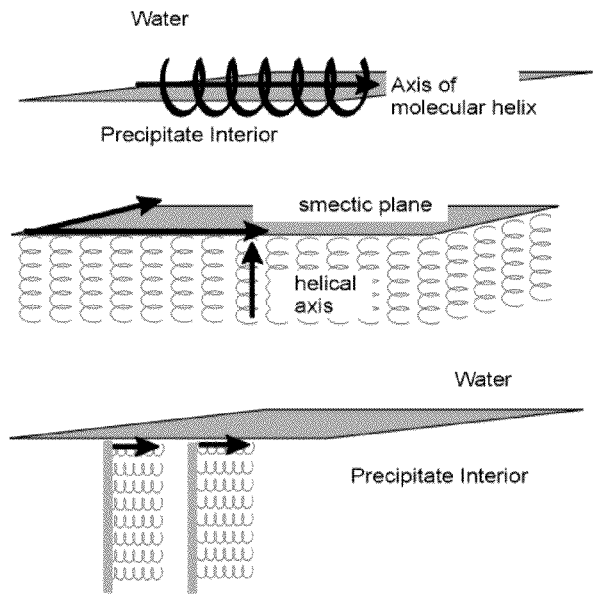
FIG. 30 depicts film morphology and helix anchoring: (a) a designed helix with a stronger hydrophobic/hydrophilic difference will be more readily stabilized and anchored parallel to the interface; (b) helical axis is perpendicular to smectic layer plane; and (c) helices which tend to be parallel to interface and film result in layers more often normal to film.
Figure 31:
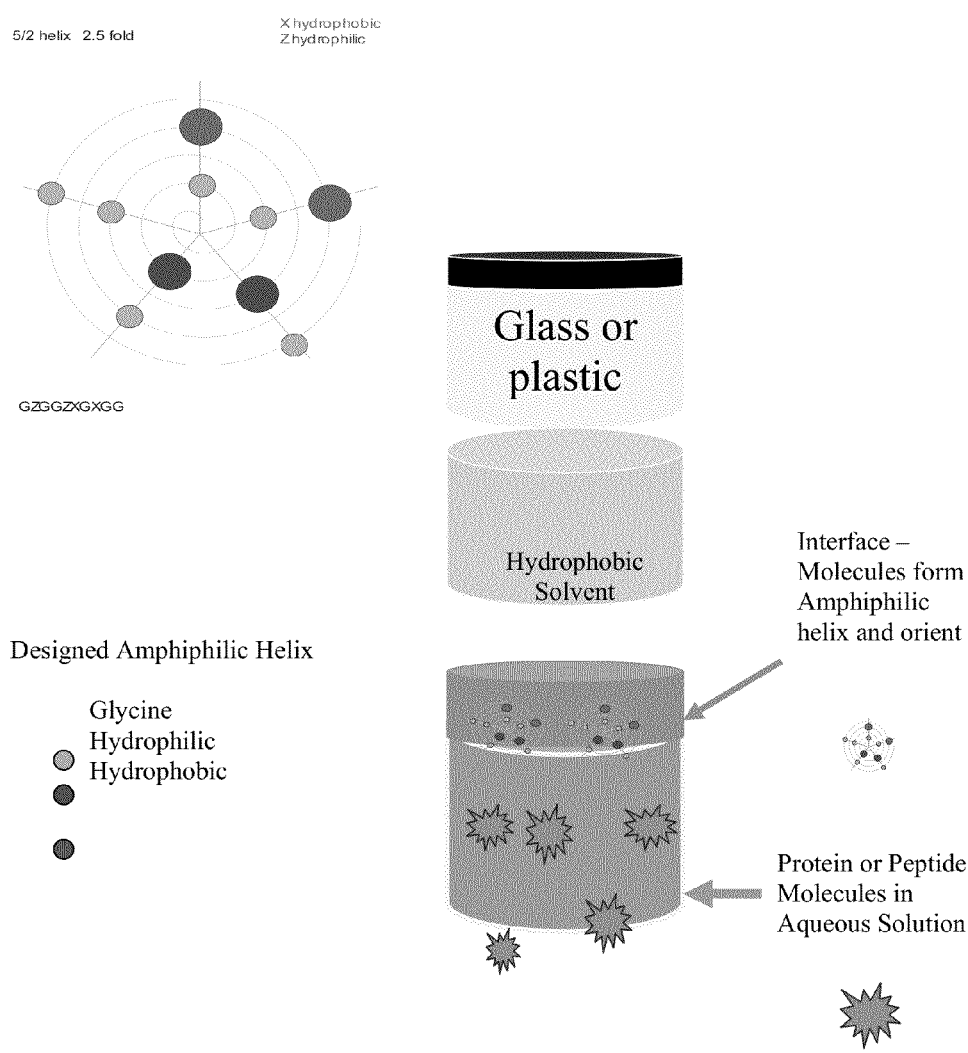
FIG. 31 depicts the templating-against-solvent technique.
Figure 32:
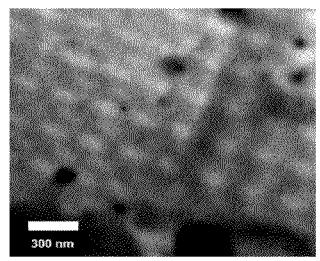
FIG. 32 depicts patterned peptide films.
Figure 32:
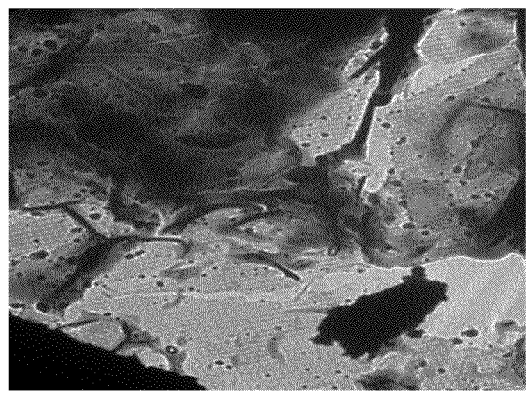
Figure 32:
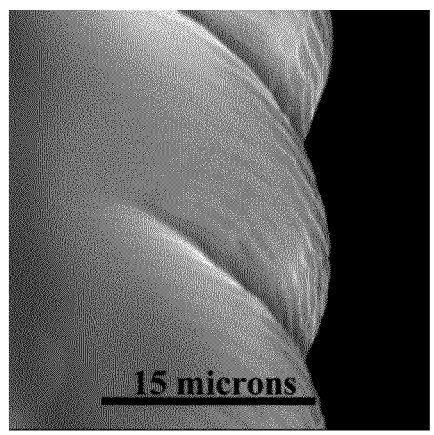
Figure 33:
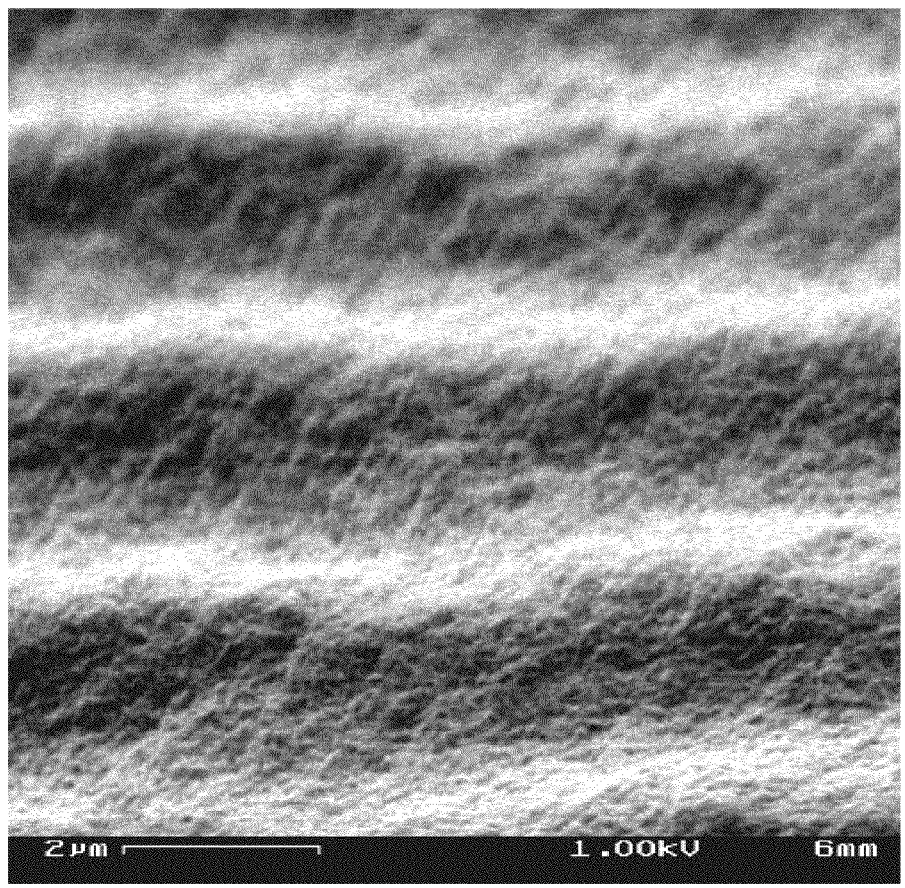
FIG. 33 depicts silk templated gels-surface "skin".

XRD—WAXD experiments were done using Bruker D8 Discover X-ray diffractometer with GADDS multiwire area detector. 40 kV and 20 mA and 0.5 mm collimator was used. The distance between the detector and the sample for WAXD was 60 mm. CuKα. Layered structures (6-12 nm layers) with Silk I secondary structures (a non integer helix between the silk II β-strand and the silk III three fold helix) were observed. The chloroform gels had high orientation in WAXS (FIG. 19).

TEM—Interfacial films of silk fibroin and the peptide were characterized using a JEOL 2000 FX-II TEM operating at 200 kV accelerating voltage. Samples were maintained at below −150° C. during the TEM characterization, utilizing a cryogenic sample holder. Working at cryogenic temperatures was necessary in order to reduce beam damage and to prevent the loss of water from hydrated crystal structures in the high vacuum of the microscope. Electron diffraction and TEM bright field imaging were used to assess the structures in the films. An internal gold standard was used to determine lattice spacings. Defocused diffraction imaging was used to determine the relative orientations of the diffraction patterns and banding or crystallite facets in the morphology images. Detection of salt contamination and the characteristics of residual salt crystallites have been described in previous papers. Valluzzi, R.; Gido, S. P. Biopolymers 1997, 42, 705-717; Valluzzi, R.; Gido, S.; Zhang, W.; Muller, W.; Kaplan, D. Macromolecules 1996, 29, 8606-8614. No salt artifacts were observed in the structures obtained from the water-hexane interface.

INCORPORATION BY REFERENCE

All of the patents, patent applications, and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of preparing a fibrous protein smectic hydrogel, comprising:
   a. contacting an aqueous fibrous protein solution with a solvent that is not miscible with water;
   b. allowing the solution in contact with the solvent to age at about room temperature or under conditions preventing evaporation or both; and
   c. collecting the resulting fibrous protein smectic hydrogel; and optionally allowing the hydrogel to dry,
   wherein the fibrous protein is selected from the group consisting of silk, collagens, keratins, actins, chorions, and seroins.

2. The method of claim 1, wherein the fibrous protein is silk.

3. The method of claim 1, wherein the fibrous protein smectic hydrogel is a bulk solid comprising several ordered layers of the fibrous protein.

4. The method of claim 1, wherein the fibrous protein solution is present in greater than or equal to 4% by weight.

5. The method of claim 4, wherein the fibrous protein is silk.

6. The method of claim 4, wherein the fibrous protein solution is present in greater than or equal to 8% by weight.

7. The method of claim 6, wherein the fibrous protein is silk.

* * * * *